United States Patent
Da Silva Ribeiro et al.

(10) Patent No.: US 10,513,697 B2
(45) Date of Patent: Dec. 24, 2019

(54) CO₂ PROFILE CULTIVATION

(71) Applicant: Hoffmann-La Roche Inc., Little Falls, NJ (US)

(72) Inventors: Betina Da Silva Ribeiro, Basel (CH); Markus Emmler, Penzberg (DE); Alexander Jockwer, Wuppertal (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/540,322

(22) Filed: Nov. 13, 2014

(65) Prior Publication Data

US 2015/0299688 A1     Oct. 22, 2015

Related U.S. Application Data

(63) Continuation of application No. 14/222,305, filed on Mar. 21, 2014, now abandoned, which is a continuation of application No. PCT/EP2012/068248, filed on Sep. 17, 2012.

(30) Foreign Application Priority Data

Sep. 21, 2011   (EP) ..................... 11182107

(51) Int. Cl.
    *C07K 16/00*     (2006.01)
    *C12N 9/88*     (2006.01)
    *C12N 1/00*     (2006.01)
    *C12P 21/02*     (2006.01)
    *C07K 1/00*     (2006.01)
    *A61K 38/00*     (2006.01)

(52) U.S. Cl.
    CPC ............... *C12N 9/88* (2013.01); *C07K 1/00* (2013.01); *C07K 16/00* (2013.01); *C12N 1/00* (2013.01); *C12P 21/02* (2013.01); *C12Y 402/01001* (2013.01)

(58) Field of Classification Search
    None
    See application file for complete search history.

(56) References Cited

U.S. PATENT DOCUMENTS

| | | | |
|---|---|---|---|
| 6,406,888 B1 | 6/2002 | Conklin et al. | |
| 6,706,524 B2 | 3/2004 | Wagner et al. | |
| 8,460,895 B2 | 11/2013 | Eisenkraetzer et al. | |
| 2002/0052046 A1 | 2/2002 | Wagner et al. | |
| 2006/0040354 A1* | 2/2006 | O'Keefe | C07K 16/00 435/69.1 |
| 2006/0257990 A1* | 11/2006 | Daigle | C12N 9/88 435/232 |
| 2010/0216201 A1* | 8/2010 | Soong | C12P 7/06 435/161 |
| 2011/0306095 A1* | 12/2011 | Jostock | C07K 16/00 435/69.6 |
| 2013/0244275 A1* | 9/2013 | Schlatter | C07K 16/00 435/69.1 |

FOREIGN PATENT DOCUMENTS

| | | |
|---|---|---|
| JP | 2007-508003 A | 4/2007 |
| JP | 2011-160802 A | 8/2011 |
| WO | 2005/035748 A1 | 4/2005 |
| WO | 2010/017338 A1 | 2/2010 |

OTHER PUBLICATIONS

Sterling et al. (2001) A transport metabolon. Functional interaction of carbonic anhydrase II and chloride/bicarbonate exchangers, J. Biol. Chem., vol. 276, pp. 47886-47894.*
Backliwal et al. (2008) Rational vector design and multi-pathway modulation of HEK 293E cells yield recombinant antibody titers exceeding 1 g/l by transient transfection under serum-free conditions, Nucleic Acid Res., vol. 36, No. 15, pp. 1-7.*
Thomas et al. (2005) "HEK293 cell line: A vehicle for the expression of recombinant proteins", J. Pharmcol. Toxicol. Meth., vol. 51, pp. 187-200.*
Dalton et al. (2014) "Over-expression of secreted proteins from mammalian cell lines", Protein Sci., vol. 23, pp. 571-525.*
Backliwal et al. (2006) Rational vector design and multi-pathway modulation of HEK 293E cells yield recombinant antibody titers exceeding 1 g/l by transient transfection under serum-free conditions, Nucleic Acid Res., vol. 36, No. 15, pp. 1-7.*
Dezengotita et al., "Effects of $CO_2$ and osmolality on hybridoma cells: growth, metabolism and monoclonal antibody production", Cytotechnology, 28:213-227 (1998).
European Search Report issued in European Patent Application No. 11182107, dated Jan. 27, 2012, in 8 pages.
Fogolin et al., Animal Cell Technology: From Target to Marker "Expression of Yeast Pyruvate Carboxylate in hGM-CSF Producing CHO Cells", E. Lindner-Olsson et al., Netherlands:Kluwer Academic Publishers,:241-243 (2001).

(Continued)

*Primary Examiner* — Manjunath N Rao
*Assistant Examiner* — Samuel W Liu
(74) *Attorney, Agent, or Firm* — Daphne Reddy

(57) ABSTRACT

A dissolved $CO_2$ change in aqueous solutions affects directly the intracellular pH (pHi) value as it does so by influencing therefore important cellular processes. The enzyme carbonic anhydrase II (CAII) catalyzes the equilibrium of $CO_2$ in aqueous solutions and because it alters the speed at which this equilibrium is reached it was identified as a strong candidate for metabolic engineering. The cell line stably expressing hCAII presented a better initial re-alkalinization of cytoplasm after induced $CO_2$ acid load. The most alkaline pHi value associated to the lowest pHi variations was observed for that cell line in long term increased $CO_2$ levels. In general, the increased $CO_2$ profile triggered the quicker progress of G0G1-cell cycle phase for both transfected and control cell lines.

10 Claims, 26 Drawing Sheets
Specification includes a Sequence Listing.

(56) References Cited

OTHER PUBLICATIONS

Fogolin et al., "Impact of temperature reduction and expression of yeast pyruvate carboxylase on hGM-CSF-producing CHO cells", Journal of Biotechnology, 109:179-191 (2004).
International Search Report issued in International Application No. PCT/EP2012/068248, 3 pages (dated Feb. 8, 2013).
Kim et al., "Functional expression of human pyruvate carboxylase for reduced lactic acid formation of Chinese hamster ovary cells (DG44)", Appl Microbiol Biotechnol, 76:659-665 (2007).
Kimura et al., "Effects of Elevated $pCO_2$ and/or Osmolality on the Growth and Recombinant tPA Production of CHO Cells", Biotechnology and Bioengineering, 52:152-160 (1996).
Pattison et al., "Measurement and Control of Dissolved Carbon Dioxide in Mammalian Cell Culture Processes Using an in Situ Fiber Optic Chemical Sensor", Biotechnol. Prog., 16(5):769-774 (2000).
Supuran, "Carbonic Anhydrases—An Overview", Current Pharmaceutical Design, 14:603-614 (2008).
Takuma et al., "Dependence on Glucose Limitation of the $pCO_2$ Influences on CHO Cell Growth, Metabolism and IgG Production", Biotechnology and Bioengineering, 97(6):1479-1488 (Aug. 15, 2007).
Yoon et al., "Enhancement of recombinant erythropoietin production in CHO cells in an incubator without CO2 addition", Cytotechnology 37:119-132 (2001).
Zhu et al., "Effects of Elevated pC02 and Osmolality on Growth of CHO Cells and Production of Antibody-Fusion Protein B1: A Case Study", Biotechnol. Prog. 21:70-77 (2005).
Li et al., "Carbonic Anhydrase II Binds to and Enhances Activity of the $Na^+/H^+$ Exchanger*". The Journal of Biological Chemistry 277(39):36085-36091 ( 2002).

\* cited by examiner

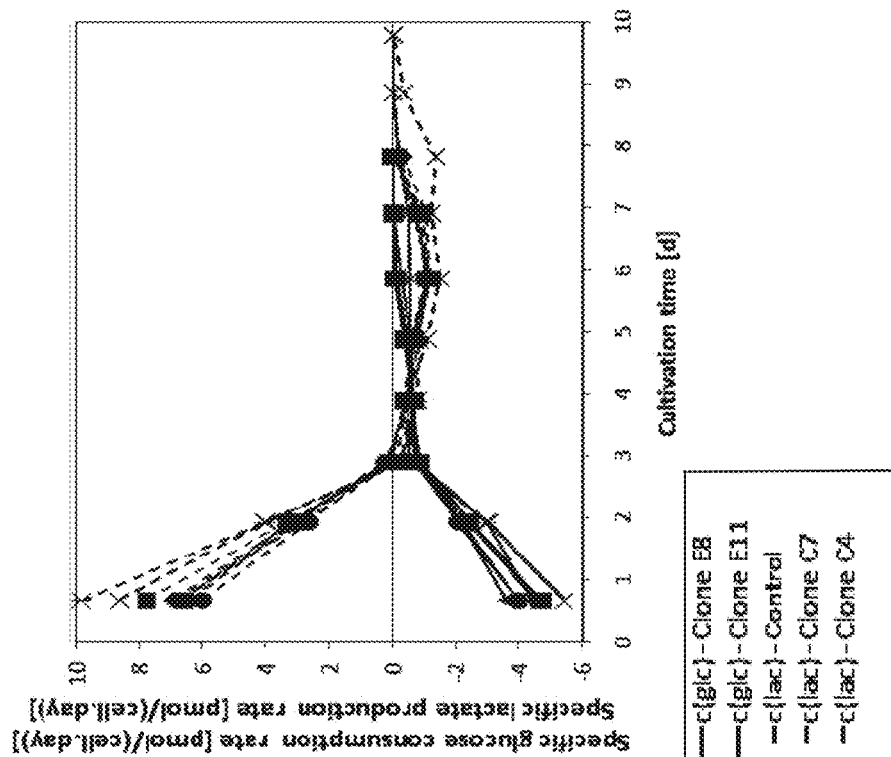
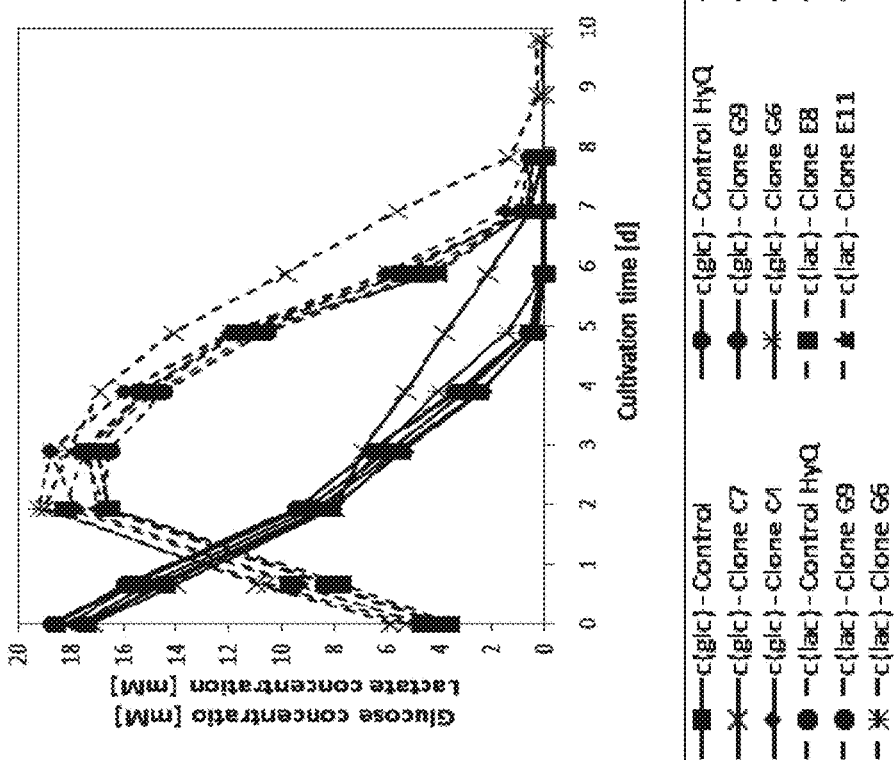
Figure 3

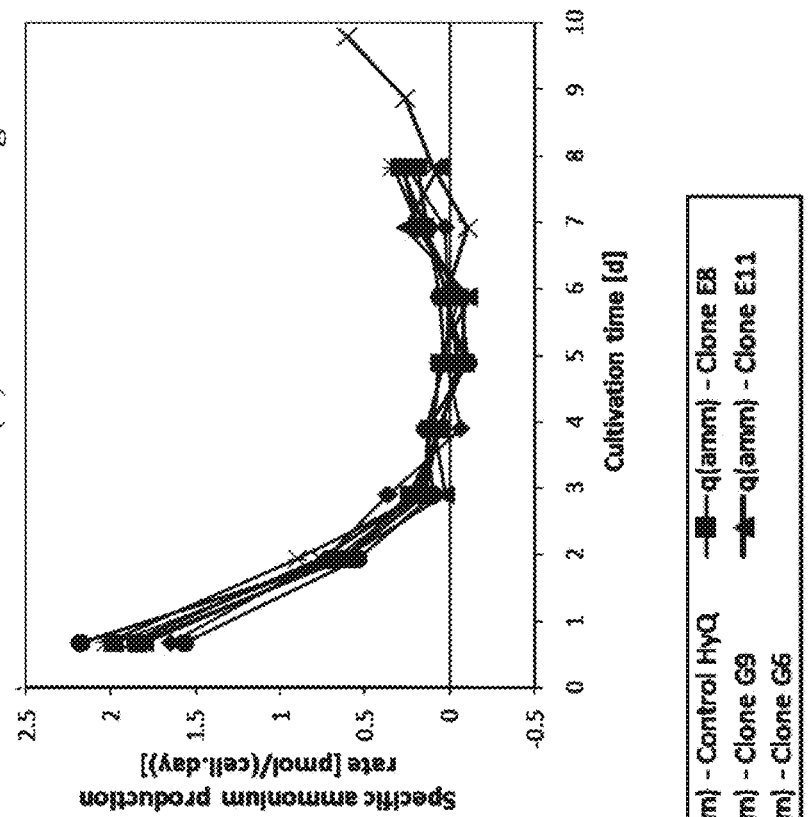
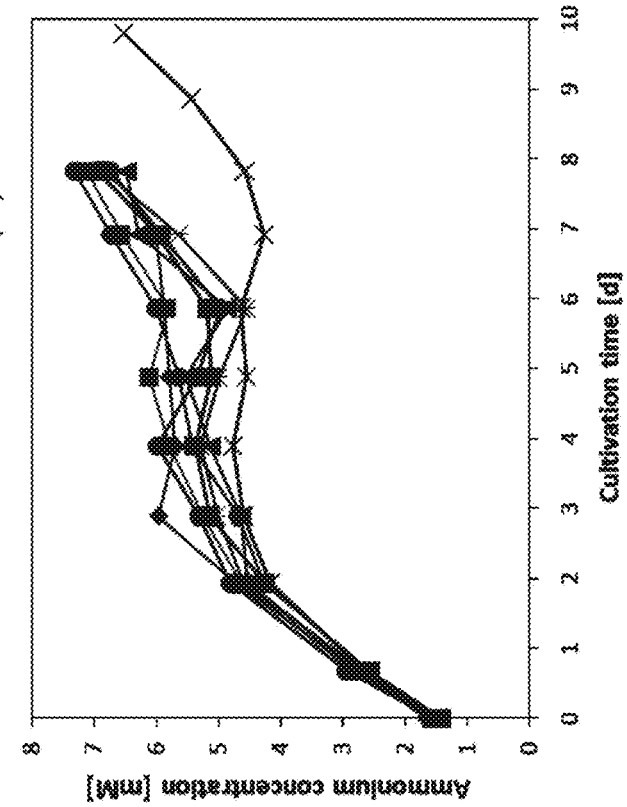
Figure 4

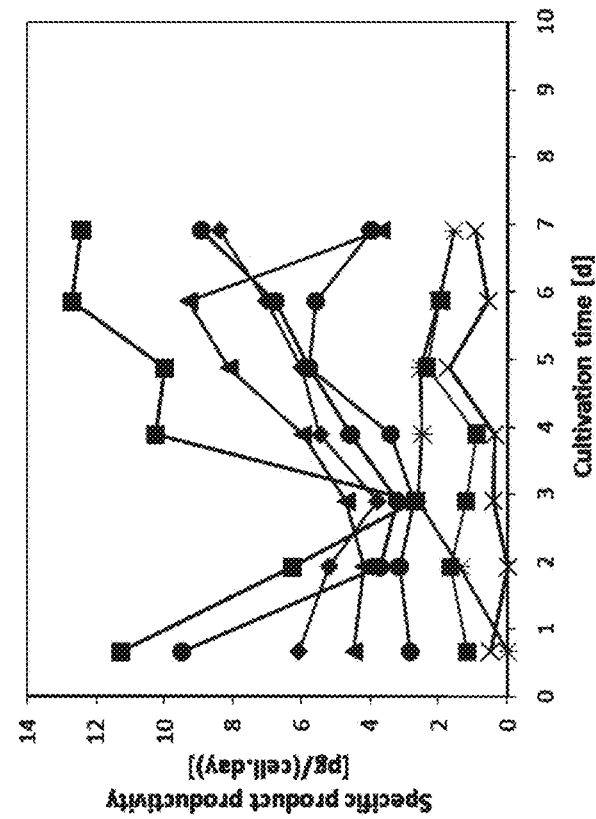
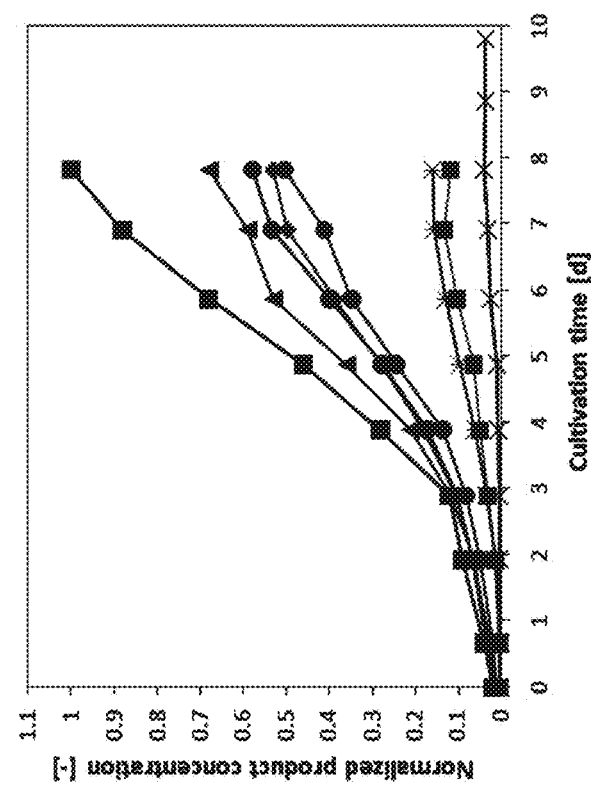
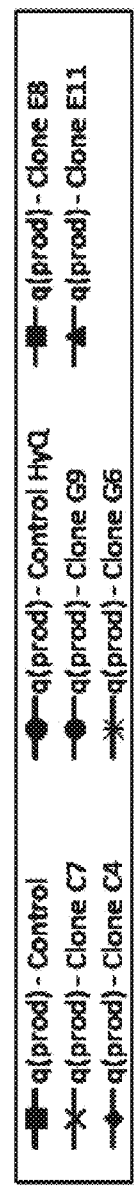
Figure 5

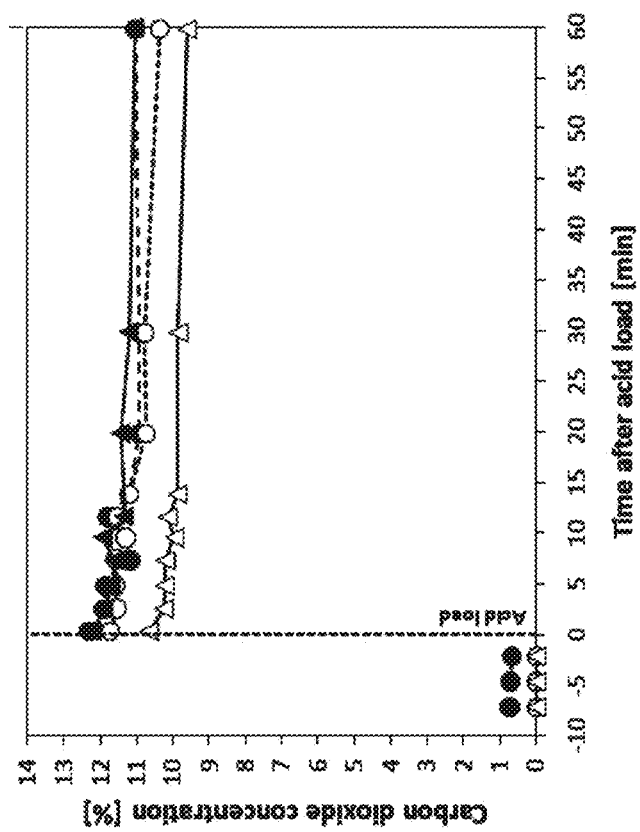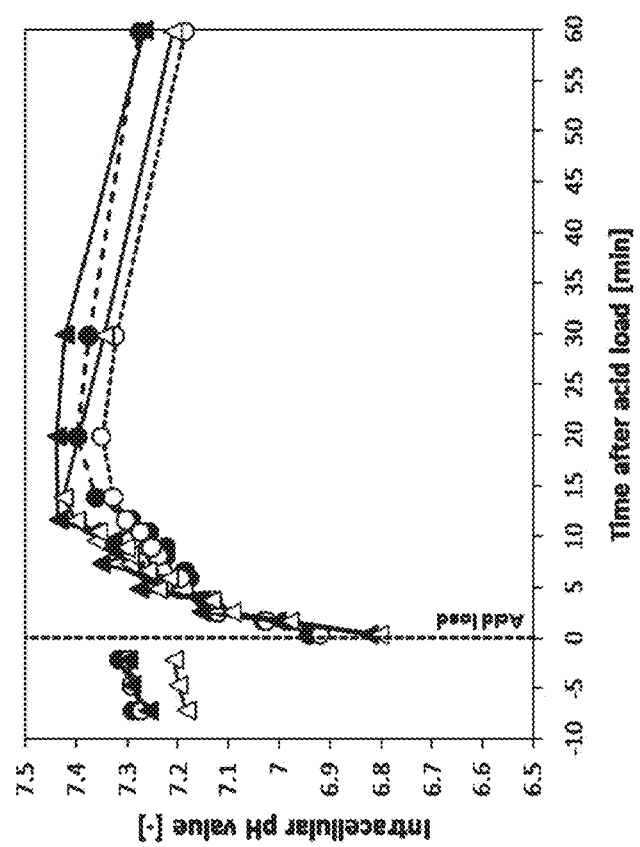
Figure 6

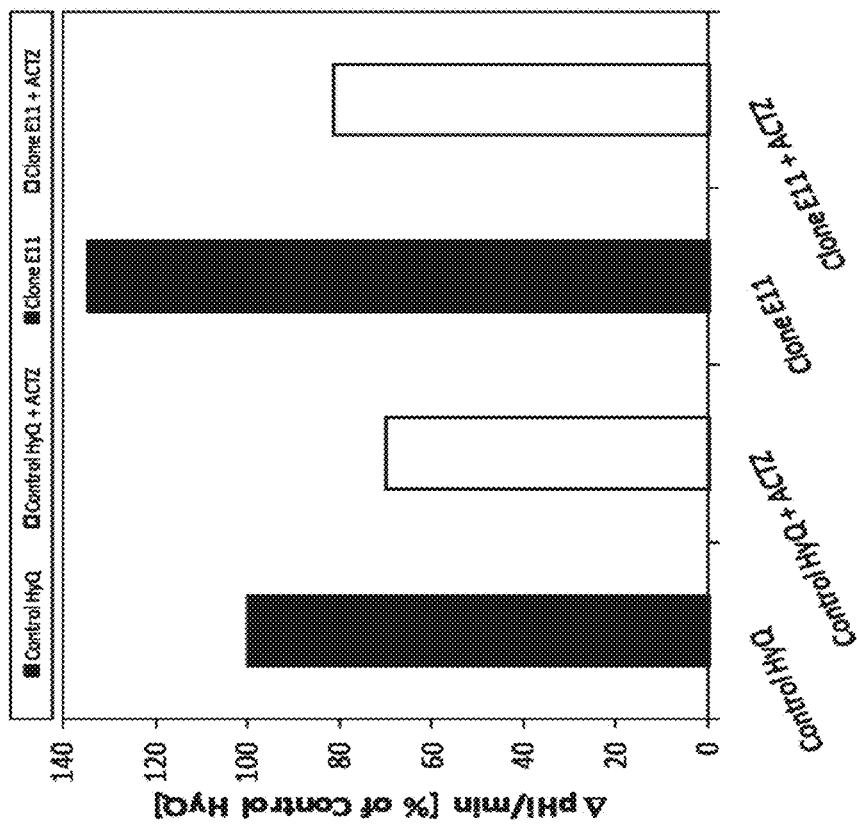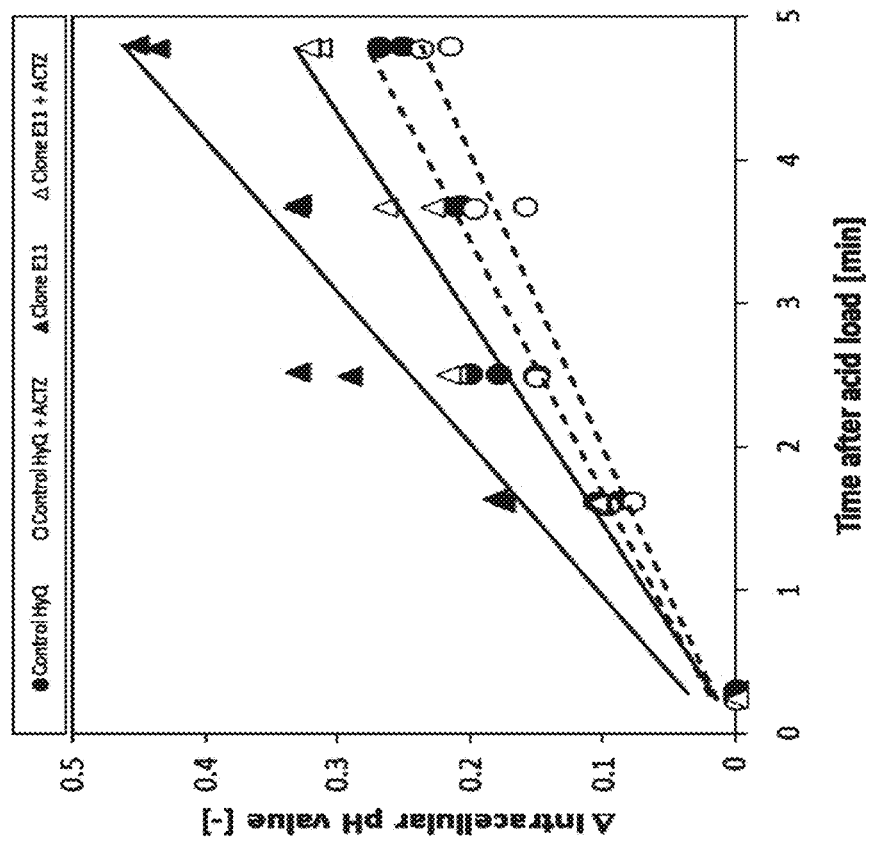
Figure 8

(B)

Figure 15
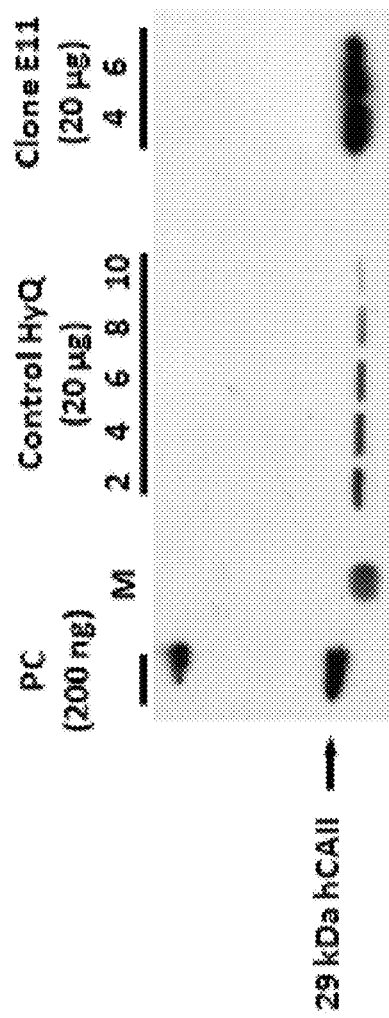
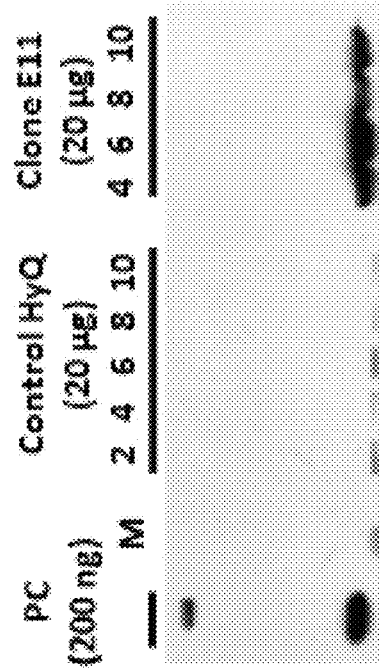

$CO_2$ PROFILE CULTIVATION

CROSS REFERENCE TO RELATED APPLICATIONS

This application is a continuation of U.S. patent application Ser. No. 14/222,305, filed on Mar. 21, 2014, which is a continuation of International Patent Application No. PCT/EP2012/068248, filed on Sep. 17, 2012, which claims priority to European Patent Application No. 11182107.0, filed on Sep. 21, 2011, the entire contents of which are incorporated herein by reference.

SEQUENCE LISTING

The instant application contains a Sequence Listing submitted via EFS-Web and hereby incorporated by reference in its entirety. Said ASCII copy, created on Oct. 29, 2014, is named P4779C2SeqList.txt, and is 7,531 bytes in size.

FIELD OF THE INVENTION

Herein is reported a genetically engineered CHO cell that has been modified in the $CO_2$ metabolism by the introduction of a nucleic acid encoding a heterologous enzyme and its use in the production of a polypeptide.

BACKGROUND OF THE INVENTION

In the recombinant production of polypeptides not only a high expression yield of the polypeptide of interest is desired, which is influenced by the entire process design, such as cell densities, productivity and product quality, but also production costs and downstream processing have to be considered.

The dissolved carbon dioxide concentration ($dCO_2$) has been identified as one of the key process parameters affecting negatively cell growth, productivity and product quality in cell culture technology. Carbon dioxide is produced by the cells themselves and can accumulate in the culture media leading to critical levels, especially in large scale industrial cultivations. The non-polar carbon dioxide molecule easily enters the cultivated cell, and is converted to bicarbonate and protons, through carbonic anhydrase. The accumulation of these protons in cytoplasm can cause acidification of the cytosol, which can in turn interfere with the optimal pH value required for cellular enzymes involved in cell growth and metabolism.

The problem of high levels of $pCO_2$ and associated high acidity plus increased osmolality associated with pH control arose and is considered to be the major difficulty encountered in scaling up mammalian cell culture to achieve high cell densities. Intracellular pH is an important modulator of the cell function. Many enzymes exhibit pH dependence in the physiological range such their activities are affected by small variations in intracellular pH. Hence, precise regulation of cytosolic pH (pHi) is a prerequisite for the normal functioning of cells [FRELIN, C., et al., Eur. J. Biochem. 174 (1988) 3-14; MADSHUS, I. H., Biochem. J. 250 (1988) 1-8; ROOS, A. AND BORON, W. F. Physiol. Rev. 61 (1981) 296-434]. Most of cells are equipped with several mechanisms to regulate pHi, which makes its regulation extremely complex.

The effect of $CO_2$ in cell culture result from the fact that, as non polar molecule, the dissolved $CO_2$ can easily pass the cell membrane and enter the cytosol and the mitochondrial compartment of a cultivated cell affecting the intracellular pH (pHi) and directly influencing important cellular processes.

Inside the cell, $CO_2$ reacts with $H_2O$ and forms $H_2CO_3$. This reaction occurs spontaneously and is also catalyzed by carbonic anhydrase enzymes (CA, carbonate hydrolyase, EC 4.2.1.1) which are zinc metalloenzymes that catalyze the interconversion of carbon dioxide and water into carbonic acid, protons and bicarbonate ions. In mammals fourteen carbonic anhydrase isoforms have so far been identified and the predominant cytoplasmic isozyme is carbonic anhydrase II (CAII) [SLY, W. S. AND HU, P. Y., Ann. Rev. Biochem. 64 (1995) 375-601].

Carbonic anhydrase is known to play a central role in the regulation of intracellular [ROOS, A. AND BORON, W. F. Physiol. Rev. 61 (1981) 296-434] and extracellular pH [CHEN, J. C. AND CHESLER, M., Proc. Natl. Acad. Sci. USA 89 (1992) 7786-7790]. Carbonic anhydrase II consists of a single polypeptide chain with 260 amino acid residues corresponding to a molecular mass of about 29 kDa. It is present in the cytosol of most tissues. Overall, MOSTAFA AND GU [MOSTAFA, S. S. AND GU, X., Biotechnol. Prog. 19 (2003) 45-51] reported an improved productivity, culture time, and final titer.

De Zengotita, V. M., et al., performed a characterization of hybridoma cell responses to elevated $pCO_2$ and osmolality (Biotechnol. Bioeng. 77 (2002) 369-380). Effects of elevated $pCO_2$ and osmolality on growth of CHO cells and production of antibody-fusion protein B1 was reported by Zhu, M. M., et al. in Biotechnol. Prog. 21 (2005) 70-77. Gray, D. R., et al. reported $CO_2$ in large-scale and high-density CHO cell perfusion culture (Cytotechnol. 22 (1996) 65-78).

SUMMARY OF THE INVENTION

Herein is reported the generation of a cell line stably transfected with a structural gene encoding a carbonic anhydrase (CA) and its use in the recombinant production of a polypeptide. The expression of a carbonic anhydrase provides for an efficient control of pHi at alkaline levels, causing a cell cycle arrest in G0G1-phase and an increase in cell-specific productivity.

One aspect as reported herein is a method for producing a polypeptide comprising the following steps
  a) cultivating a mammalian cell comprising a first nucleic acid encoding a carbonic anhydrase and a second nucleic acid encoding the polypeptide in a cultivation medium, and
  b) recovering the polypeptide from the cell or the cultivation medium and thereby producing the polypeptide.

In one embodiment the cultivating is for a first period of time with a first constant $pCO_2$ value, and thereafter for a second period of time with an increasing $pCO_2$ value from the first $pCO_2$ value to a second $pCO_2$ value.

In one embodiment the cultivating is further for a third period of time after the second period of time with the second $pCO_2$ value held constant.

In one embodiment the first constant $pCO_2$ value is of from about 4% to about 9%. In one embodiment the first constant $pCO_2$ value is about 5%.

In one embodiment the second $pCO_2$ value is of from about 15% to about 30%. In one embodiment the second $pCO_2$ value is about 25%.

In one embodiment the carbonic anhydrase is a carbonic anhydrase II or a carbonic anhydrase V.

In one embodiment the carbonic anhydrase is human carbonic anhydrase II or human carbonic anhydrase V.

In one embodiment the carbonic anhydrase has the amino acid sequence of SEQ ID NO: 03.

In one embodiment the first nucleic acid is stably integrated in the genome of the mammalian cell.

In one embodiment the polypeptide is an antibody, or an antibody conjugate, or an antibody fragment, or an Fc-region fusion polypeptide.

In one embodiment the mammalian cell is a CHO cell. In one embodiment the CHO cell is a CHO K1 cell.

One aspect as reported herein is a CHO cell comprising a first nucleic acid encoding human carbonic anhydrase II or a variant thereof and a second nucleic acid encoding an antibody, or an antibody conjugate, or an antibody fragment, or an Fc-region fusion polypeptide.

One aspect as reported herein is a method for producing a polypeptide comprising the following steps
 a) cultivating a mammalian cell comprising a nucleic acid encoding the polypeptide in a cultivation medium, and
 b) recovering the polypeptide from the cell or the cultivation medium and thereby producing the polypeptide,
 whereby the cultivating is for a first period of time with a first constant $pCO_2$ value, and thereafter for a second period of time with an increasing $pCO_2$ value from the first $pCO_2$ value to a second $pCO_2$ value.

In one embodiment the mammalian cell comprises a nucleic acid encoding human carbonic anhydrase. In one embodiment the carbonic anhydrase is human carbonic anhydrase II or human carbonic anhydrase V.

In one embodiment the cultivating is further for a third period of time after the second period of time with the second $pCO_2$ value held constant.

In one embodiment the first constant $pCO_2$ value is of from about 4% to about 9%. In one embodiment the first constant $pCO_2$ value is about 5%.

In one embodiment the second $pCO_2$ value is of from about 15% to about 30%. In one embodiment the second $pCO_2$ value is about 25%.

DETAILED DESCRIPTION OF THE INVENTION

Herein is reported the generation of a cell line stably transfected with a structural gene encoding human carbonic anhydrase II (hCAII).

It has been found that the selection of a cell line producing a recombinant polypeptide can be made not only based on growth, productivity and metabolic data, but also on the expression and enzyme kinetics of the hCAII enzyme.

It has also been found that a cell stably transfected with a nucleic acid encoding and expressing hCAII has different characteristics when cultivated under different pCO2 profiles, such as a constant $pCO_2$ and a slowly increasing $pCO_2$.

The term "about" denotes that the thereafter following value is no exact value but is the center point of a range that is in one embodiment +/−10% of the value, or in one embodiment +/−5% of the value, or in one embodiment +/−2% of the value, or in one embodiment +/−1% of the value. If the value is a relative value given in percentages the term "about" also denotes that the thereafter following value is no exact value but is the center point of a range that is in one embodiment +/−10% of the value, or in one embodiment +/−5% of the value, or in one embodiment +/−2% of the value, or in one embodiment +/−1% of the value, whereby the upper limit of the range cannot exceed a value of 100%.

The term "antibody" is used herein in the broadest sense and encompasses various antibody structures, including but not limited to monoclonal antibodies, polyclonal antibodies, multispecific antibodies (e.g., bispecific antibodies), and fragments so long as they exhibit the desired antigen-binding activity. An antibody in general comprises two so called light chain polypeptides (light chain) and two so called heavy chain polypeptides (heavy chain). Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of an antibody's light or heavy chain in turn comprises different segments, i.e. four framework regions (FR) and three hypervariable regions (CDR).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

The term "Fc-region" herein is used to define a C-terminal region of an antibody heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242.

The "Fc-region" of an antibody is not involved directly in binding to the antibody's antigen, but exhibit various effector functions. Depending on the amino acid sequence of the constant region of the heavy chains, antibodies (immunoglobulins) are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the immunoglobulin class to which an antibody belongs are the heavy chain constant regions of immunoglobulins are called α (IgA), δ (IgD), ε (IgE), γ (IgG), and μ. (IgM), respectively. The antibodies according to the invention belong preferably to the IgG class. An "Fc-region of an antibody" is a term well known to the skilled artisan and defined on basis of the papain cleavage of antibodies. The antibodies according to the invention contain as Fc-region a human Fc-region or an Fc-region derived from human origin. In one embodiment the Fc-region is either an Fc-region of a human antibody of the subclass IgG4 or an Fc-region of a human antibody of the subclass IgG1, IgG2, or IgG3, which is modified in such a way that no Fcγ receptor (e.g. FcγRIIIa) binding and/or no C1q binding as defined below can be detected. Preferably the Fc-region is a human Fc-region and especially preferred either from human IgG4 subclass or a mutated Fc-region from human IgG1 subclass. Further preferred are Fc-regions from human IgG1 subclass with mutations L234A and L235A. While IgG4 shows reduced Fcγ receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, or/and His435 are residues which, if altered, provide also reduced Fcγ receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434). Preferably an antibody according to the invention is in regard to Fcγ receptor binding of IgG4 subclass or of IgG1 or IgG2 subclass, with a mutation in L234, L235, and/or D265, and/or contains the PVA236 mutation. Preferred are the mutations S228P, L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA). Especially preferred are the mutations S228P of IgG4, and L234A and L235A of IgG1. The Fc-region of an antibody is directly involved in ADCC (antibody-dependent cell-mediated cytotoxicity) and CDC (complement-dependent cytotoxicity). An antibody which does not bind Fcγ receptor and/or complement factor C1q does not elicit antibody-dependent cellular cytotoxicity (ADCC) and/or complement dependent cytotoxicity (CDC).

As used herein the term "Fc-region derived from human origin" denotes an Fc-region which is either an Fc-region of a human antibody of the subclass IgG4 or an Fc-region of a human antibody of the subclass IgG1, IgG2, or IgG3, including mutated forms thereof. Preferably the Fc-region of a human antibody of the subclass IgG1, IgG2, or IgG3 is modified in such a way that no Fcγ receptor (FcγR, i.e. FcγRIIIa) binding and/or no C1q binding as defined below can be detected. An "Fc-region of an antibody" is a term well known to the skilled artisan and defined on the basis of papain cleavage of antibodies. The antibodies according to the invention contain as Fc-region an Fc-region derived from human origin and preferably all other parts of the human constant region. Preferably the Fc-region is a human Fc-region and especially preferred either from human IgG4 subclass, or from human IgG1 subclass, or a mutated Fc-region from human IgG1 subclass. Mostly preferred are the Fc-regions and heavy chain constant region shown in SEQ ID NO: 3, SEQ ID NO: 4, SEQ ID NO: 3 with mutations L234A and L235A, SEQ ID NO: 4 with mutation S228P.

The terms "cell" and "cell line" are used interchangeably and refer to cells into which exogenous nucleic acid has been introduced, including the progeny of such cells. Cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "cell" includes both prokaryotic cells, which are used for propagation of plasmids, and eukaryotic cells, which are used for the expression of a nucleic acid. In one embodiment the cell is a mammalian cell. In one embodiment the mammalian cell is selected from the group of mammalian cells comprising CHO cells (e.g. CHO K1, CHO DG44), BHK cells, NS0 cells, SP2/0 cells, HEK 293 cells, HEK 293 EBNA cells, PER.C6® cells, and COS cells.

A "nucleic acid" as used herein, refers to a polymeric molecule consisting of individual nucleotides (also called bases) a, c, g, and t (or u in RNA), for example to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid, or the chromosome of a host cell. A nucleic acid is likewise characterized by its nucleic acid sequence consisting of individual nucleotides.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

A "nucleic acid" or "nucleic acid sequence" as used herein refers to a naturally occurring or partially or fully non-naturally occurring nucleic acid encoding a polypeptide which can be produced recombinantly. The nucleic acid can be build up of DNA-fragments which are either isolated or synthesized by chemical means. The nucleic acid can be integrated into another nucleic acid, e.g. in an expression plasmid or the genome/chromosome of a eukaryotic host cell. Plasmid includes shuttle and expression plasmids. Typically, the plasmid will also comprise a prokaryotic propagation unit comprising an origin of replication (e.g. the ColE1 origin of replication) and a selectable marker (e.g. ampicillin or tetracycline resistance gene), for replication and selection, respectively, of the plasmid in prokaryotes.

An "expression plasmid" is a nucleic acid providing all required elements for the expression of the comprised structural gene(s) in a host cell. Typically, an expression plasmid comprises a prokaryotic plasmid propagation unit, e.g. for *E. coli*, comprising an origin of replication, and a selectable marker, an eukaryotic selection marker, and one or more expression cassettes for the expression of the structural gene(s) of interest each comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

A "polypeptide" is a polymer consisting of amino acids joined by peptide bonds, whether produced naturally or synthetically. Polypeptides of less than about 20 amino acid residues may be referred to as "peptides", whereas molecules consisting of two or more polypeptides or comprising one polypeptide of more than 100 amino acid residues may be referred to as "proteins". A polypeptide may also comprise non-amino acid components, such as carbohydrate groups, metal ions, or carboxylic acid esters. The non-amino acid components may be added by the cell, in which the polypeptide is expressed, and may vary with the type of cell. Polypeptides are defined herein in terms of their amino acid backbone structure or the nucleic acid encoding the same.

Additions such as carbohydrate groups are generally not specified, but may be present nonetheless.

Recombinant production of immunoglobulins is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

As known to a person skilled in the art enables the use of recombinant DNA technology the production of numerous derivatives of a nucleic acid and/or polypeptide. Such derivatives can, for example, be modified in one individual or several positions by substitution, alteration, exchange, deletion, or insertion. The modification or derivatisation can, for example, be carried out by means of site directed mutagenesis. Such modifications can easily be carried out by a person skilled in the art (see e.g. Sambrook, J., et al., Molecular Cloning: A Laboratory Manual, Cold Spring Harbor Laboratory Press, New York, USA (1999)). The use of recombinant technology enables a person skilled in the art to transform various host cells with heterologous nucleic acid(s). Although the transcription and translation, i.e. expression, machinery of different cells use the same elements, cells belonging to different species may have among other things a different so-called codon usage. Thereby identical polypeptides (with respect to amino acid sequence) may be encoded by different nucleic acid(s). Also, due to the degeneracy of the genetic code, different nucleic acids may encode the same polypeptide.

The use of recombinant DNA technology enables the production of numerous derivatives of a nucleic acid and/or polypeptide. Such derivatives can, for example, be modified in one individual or several positions by substitution, alteration, exchange, deletion, or insertion. The modification or derivatisation can, for example, be carried out by means of site directed mutagenesis. Such modifications can easily be carried out by a person skilled in the art (see e.g. Sambrook, J., et al., Molecular Cloning: A Laboratory Manual, Cold Spring Harbor Laboratory Press, New York, USA (1999); Hames, B. D., and Higgins, S. G., Nucleic Acid Hybridization—A Practical Approach, IRL Press, Oxford, England (1985)).

The use of recombinant technology enables the transformation of various host cells with heterologous nucleic acid(s). Although the transcription and translation, i.e. expression, machinery of different cells use the same elements, cells belonging to different species may have among other things a different so-called codon usage. Thereby identical polypeptides (with respect to amino acid sequence) may be encoded by different nucleic acid(s). Also, due to the degeneracy of the genetic code, different nucleic acids may encode the same polypeptide.

Human Carbonic Anhydrase II

The hCAII encoding nucleic acid sequence was taken from the Data Bank NCBI entry NM000067 (SEQ ID NO: 01).

The human carbonic anhydrase used herein is a mutant of the wild-type human CAII (SEQ ID NO: 02) with the mutation S2A (SEQ ID NO: 03).

CHO Cell Line Recombinantly Expressing Human Carbonic Anhydrase II

The non-transfected parental cell line was cultivated as a reference in selective culture medium until no further growth could be observed. At this point the selection procedure had been completed. During the clone screening, the clones and the Control HyQ cell line were maintained in HyQ medium for about 1.5 months. Methotrexate was not included in this medium. The selected transfected cells were always cultured in medium containing methotrexate.

Expression analysis was performed as immunoblot, such as Western blot, using polyclonal anti-CAII antibody for detection and the commercially available hCAII from Sigma as control.

Seven single clones were obtained whereof five were classified as high-hCAII expressing cell lines (clones P03-E8, C7, G9, P01-E8 and E11) and the other two as low-hCAII expressing cell lines (Clones C4 and G6).

Metabolic Characterization of the Clonal Cell Lines

All values are normalized, whereby the value of the non-transfected parental cell line (=control) on cultivation day 5 denotes 100%. The growth characteristics of the different cell clones and the control are shown in FIG. 2. The term Control HyQ denotes that the non-transfected parental control cell line was grown in HyQ medium.

The parental cell line's and the clonal cell lines' metabolic parameters are shown in FIGS. 3 to 5. The maximum lactate concentration in the cultivation of the control cell line was 16 mM on cultivation day 3, while for the clonal cell lines the concentration was between 17.4 mM and 19.3 mM on cultivation days 3 and 4. The cell specific initial consumption rates were for glucose between 3.6 pmol/cell/day (Clone E11) and 4.7 pmol/cell/day (Clone E8). The corresponding values for the control cell line and the control cell line in HyQ medium were 4.7 and 4.0 pmol/cell/day, respectively. The initial cell specific production rates for lactate were between 6.0 pmol/cell/day (Clone G9) and 9.9 pmol/cell/day (Clone G6) and the control cell line and the control cell line in HyQ medium were 4.7 and 4.0 pmol/cell/day, respectively. The ammonium concentration reached final concentrations between 6.5 mM (clone E11) and 7.3 mM (clone G9). The initial cell specific ammonium production rates were between 1.57 pmol/cell/day (Clone G9) and 2.03 pmol/cell/day (Clone G6), the values for the control cell line and the control cell line in HyQ medium were 2.18 pmol/cell/day and 1.84 pmol/cell/day, respectively. After cultivation day 3, the product concentration increased linearly with time until day 7 in all cultures. The maximum product concentration was reached for the control cell line at the end of the batch culture. With respect thereto 58% product was produced by the control cell line in HyQ medium, whereas product concentrations of 68%, 53% and 50% were achieved by Clones E11, C4 and G9, respectively. The maximum cell specific production rate was 12.7 pg/cell/day for the control cell line at day 6. The control cell line in HyQ medium and clones E11, C4 and G9 had maximum cell specific production rates of 8.9 pg/cell/day (at day 7), 9.3 pg/cell/day (at day 6), 8.4 pg/cell/day (at day 7) and 5.8 pg/cell/day (at day 5), respectively.

To determine the activity of the cloned human carbonic anhydrase II values of hCAII activity were determined from the $^{18}$O-exchange data obtained by mass spectrometry. Through the titration curve of the hCAII positive control solution with the tight inhibitor ethoxyzolamide (EZA) an hCAII concentration of 1.33 μM was calculated. The determined activity of the non-inhibited positive control was 28,700 units. Human carbonic anhydrase II activity was detected in the hCAII stably transfected cell clone G9 and E11 cell lysates in RIPA buffer with activities of 201 and 241 units, respectively. The calculated hCAII concentrations were of 2.28 nM (clone G9) and 2.73 nM (Clone E11). Lysates from protein extraction by mechanical disruption provided hCAII activity only for clone E11 with 1,235 units, corresponding to an hCAII concentration of 14.0 nM. None of both extraction methods provided detectable CAII activity in the control cell line or in the control cell line in HyQ medium.

The presence of the human carbonic anhydrase II was detected by immunoblot analysis for all examined cell clones. The size of the detected protein was of 29 kDa. The expected size for the human CAII is 29,246 Da (SwissProt hCAII Ref No P00918). The different expression levels were distinguishable by the different bands thickness. This difference arises from the additional expression of the exogenous human CAII since no detection was achieved for the endogenous hamster carbonic anhydrase II (haCAII).

Herein is reported as an aspect a method for the selection of a cell stably expressing a carbonic anhydrase for use in the recombinant production of a polypeptide comprising at least one of the following steps:
  selecting a cell with maximum obtained cell density and mean specific growth rate of not less than 70% of that of the parent cell in a shaker flask cultivation; and/or
  selecting a cell which has a specific product production rate that is day 5 or 6 higher than at day 3 or 4 in a cultivation without applied selection pressure; and/or
  selecting a cell that has the highest carbonic anhydrase activity in an $^{18}O$—$CO_2$—$H_2O$-exchange determination method.

The parent cell is the cell into which the nucleic acid encoding the carbonic anhydrase has been transfected and which is subjected to the selection method as reported herein or which is used in the production method as reported herein.

In one embodiment the maximum obtained cell density and the mean specific growth rate are not less than 80% of that of the parent cell. In one embodiment the maximum obtained cell density and the mean specific growth rate are not less than 90% of that of the parent cell. In one embodiment the maximum obtained cell density and the mean specific growth rate are not less than 95% of that of the parent cell.

In one embodiment the shaker flask cultivation is for 7 to 10 days.

In one embodiment the specific product production rate that is at day 5 higher than at day 3.

In one embodiment the carbonic anhydrase activity is determined at chemical equilibrium.

The cell is in one embodiment a CHO cell, or a BHK cell, or a HEK cell, or a Sp2/0 cell.

The carbonic anhydrase is in one embodiment a human carbonic anhydrase. In one embodiment the carbonic anhydrase is carbonic anhydrase II.

Cultivation of Human Carbonic Anhydrase II Expressing Clonal Cell Lines

The hCAII-expressing cell clone E11 was cultivated with different CO2 profiles. The cultivation medium contained galactose and, thus, the produced lactate was re-metabolized.

To examine the effect of hCAII expression on the cell internal pH value (pHi), the control cell line in HyQ medium and clone E11 were submitted to a short term acidification. This was achieved by mixing the cells with a $CO_2$-containing solution and measuring the subsequent pHi recovery. FIG. 6(A) shows the course of the pHi value for clone E11 and control cell line in HyQ medium; FIG. 6(B) shows the corresponding $CO_2$ concentration during the experiment. A replicate of this experiment was performed with the carbonic anhydrase II inhibitor ethoxyzolamide and the results are presented in FIGS. 7(A) and 7(B). The initial rate of recovery and the results normalized for Control HyQ are demonstrated in FIGS. 8(A) and 8(B). The following Table summarizes some of the characteristics of the tested cell lines.

TABLE

| | Control HyQ | Clone E11 | Control HyQ + ACTZ | Clone E11 + ACTZ |
|---|---|---|---|---|
| $pH_e$ | 7.18 | 7.18 | 7.10 | 7.11 |
| Steady state pHi | 7.29 | 7.24 | 7.02 | 6.87 |
| $pH_i$ (acid load) | 6.93 | 6.81 | 6.84 | 6.61 |
| $pH_i$/min (5 min) | 0.070 | 0.094 | 0.049 | 0.057 |
| $r^2$ | 0.934 | 0.938 | 0.947 | 0.959 |

Clone E11 showed a faster pHi change compared to the control cell line in HyQ medium. An increase of the pHi value above the steady state value was observed 8 min. after acid load for clone E11 (up to pH 7.4) as opposed to 11 min. for control cell line in HyQ medium without inhibitor. For the hCAII inhibited reactions, the steady state was exceeded 5 min. after exposure of cells to $CO_2$-containing medium for both cell lines. Sixty minutes after cytoplasm acidification, the steady state was restored.

Carbon dioxide and extracellular pH were maintained constant during all experiment due to the closed system used. In the experiment without inhibitor, the transient acid load brought the cells in contact with approx. 12% $CO_2$, except for test number 2 for clone E11 (11% $CO_2$). For the hCAII inhibited experiments, this value was about 9% $CO_2$.

The recovery rates of the cells were calculated for the linear response of the first 5 min. after acid load. In this period of time, the clone E11 revealed a 34% increased initial recovery rate, compared to the control cell line in HyQ medium. The same could be seen in the presence of the hCAII inhibitor. A 30% and 19% decrease on the re-alkalinization rates were calculated for the control cell line in HyQ medium and clone E11, respectively, in the presence of the inhibitor.

With acidification of cells by ammonium chloride in the absence of $HCO^-_3$, there was no difference in the rate of recovery between the cells with or without hCAII.

In large scale cultivations, many parameters play an important role in culture performance that does not exist on bench top scale. The carbon dioxide distribution is one of these parameters and its accumulation to non-physiological levels might have a negative impact on cells.

Only limited data for mixing times at very low power inputs for large scale cultivations is available. Mixing times typically of 100 sec. (ranging from just greater than 200 sec. to approx. 70 sec.) for an 8000 l bioreactor for cell culture medium are reported (see e.g. NIENOW, A. W., et al., Cytotechnol. 22 (1996) 87-94). Thus, in a large scale bioreactor, the cells may experiment different $CO_2$ conditions due to hydrostatic pressure. Therefore, a higher re-alkalinization rate, such as that of clone E11, may be advantageous where mixing times are around 1-2 min., although the pHi variation is higher.

Parallel batch cultivations were performed. Employed were cultivation conditions with an increasing $CO_2$ level and a constant (physiological) $CO_2$ level. Until day 2, both cultivation conditions comprised a cultivation at a constant $pCO_2$ level of 5% $CO_2$. Thereafter in one cultivation a profile was imposed with increasing $pCO_2$ level from 5% to 25% within 4 days. The respective other cultivation was maintained at 5% $CO_2$. The cultivation data is shown in FIGS. 9 and 10.

The viable cell densities were normalized to the maximum cell density obtained in the control cell line at cultivation day 4. The osmolality was corrected with a NaCl solution after day 4.

The long-term controlled carbon dioxide increase had an effect on the recombinant protein production (see FIG. 11). The product concentration was normalized to the final product concentration reached by the control cell line in HyQ medium Control the controlled $CO_2$ cultivation at the end of the batch. Clone E11 showed an increased product concentration in the cultivation process. The cell specific productivity was increased for both cell lines at increased/increasing $CO_2$ levels.

The influence of the different $CO_2$ profiles on the glucose consumption and lactate production are illustrated in FIG. 12. For the hCAII-expressing clone E11, 27.5 mM and 26.3 mM of lactate were determined at day 3 for the constant 5% and the increased $CO_2$ level cultivation, respectively. At the end of the batch culture, ammonium concentrations determined were of about 6 mM.

The pseudo-null method was applied for flow cytometric measurements of the intracellular pH value during the cultivation process. The culture extracellular pH was controlled to pH 7.2. The results for all cultivations are illustrated in FIG. 13. For all four cultivations, the initial intracellular pH value was between pH 7.26 and pH 7.29. Subsequently, the pH value decreases to pH values below the extracellular pH value of the cultivation. When the profile reached its $CO_2$ maximum value of 25% (cultivation day 6), the pHi reached a value of 7.2. The clone E11 reference culture (5% $CO_2$) presented a pHi value of 7.14 at cultivation day 5. At cultivation day 5 a difference of 0.16 pH units was calculated for the long term increased $CO_2$ cultures. The metabolic engineered cell line was able to maintain higher intracellular pH values during long term $CO_2$ increase cultivation with controlled extracellular pH value.

The percentage of cells in G0G1- and S-phases for batch cultures of both control cell line and hCAII-transfected cell line at controlled 5% $CO_2$ and $CO_2$ profile are illustrated in FIG. 14. The proportion of cells in the G0G1-phase started between 25% and 30%, whereas the fraction of cells in the S-phase started at about 47%. The amount of cells in the S-phase maintained very high during the exponential growth phase (between 40% and 50%). For clone E11 cultured with a $CO_2$ profile an increase of the percentage of cells in the G0G1-phase occurred after cultivation day 4, up to 65% four days later. For the control cell line in HyQ medium an increase occurred after day 5, up to 49% at day 8. The fraction of cells on the S-phase decreased reaching 20% for clone E11 and 34% for control cell line in HyQ medium, respectively. An increased $CO_2$ profile from 5% to 25% $CO_2$ triggers the cells to enter earlier in the G0G1-phase.

The transfected cells showed a stable hCAII expression during the cultivations (constant and profile, FIG. 15).

By increasing the $pCO_2$ levels in a controlled manner, an efficient control of pHi at alkaline levels, causing a cell cycle arrest in G0G1-phase and an increase in cell-specific productivity was achieved.

It could be shown that the final product concentration was increased by 11% and the overall cultivation time was increased by 1 day for clone E11 cell line with increasing $pCO_2$ levels.

The glycosylation profile of the human carbonic anhydrase II expressing cell line was compared with the one obtained from the original cell line. Samples taken at the end of the bioreactor cultures at different controlled $CO_2$ levels of clone E11 and Control HyQ were analyzed and the results are shown in FIG. 16.

The relative amount of digalactosylated (G2) and mannose structures were below 15% and 10% respectively of total glycosylation for all cultivations. The total amount of galactosylated structures showed a difference of 10% between clone E11 cultivated at increased $CO_2$ levels and the control cell line in HyQ medium cultivated at 5% $CO_2$.

During all cultivations the pHe was controlled to pH 7.2 pH and the pHi ranged between 7.01 and 7.31.

SUMMARY OF THE INVENTION

Generation of an hCAII Expressing Cell Line
    short screening procedure; resulting clones show no effect on cell growth, metabolism or glycosylation in batch cultures compared to parent cell line
    production of active hCAII enzyme through linear DNA transfection of hCAII gene in a CHO cell line Physiologic Effect of CAII on pHi
    faster re-alkalization of cytoplasm associated to higher initial recovery rates after $CO_2$ acid load for hCAII expressing cell line
    the presence of hCAII might have an influence in the short-term pH recovery under industrial mammalian cell culture conditions, especially at large cultivation volumes
    more alkaline pHi for hCAII expressing cell under CO2 profile cultivation indicating a positive action of the hCAII enzyme with respect to efficient re-alkalization of the cell's cytoplasm Long-Term CO2 Increase on Cells
    change of the cell growth of the hCAII expressing cell line in the presence of a $CO_2$ profile
    smallest pHi variations and more alkaline pHi value in the presence of a $CO_2$ profile for the hCAII expressing cell line
    entrance in the G0G1-phase of the cell cycle with associated higher specific productivity for clonal cell line and control cell line with a $CO_2$ profile
    hCAII expressing cell entered earlier in the G0G1-phase and the increase of the fraction of cells in this phase was earlier compared to non-hCAII expressing cells Outlook
    In order to take advantage of the long term alkaline pHi and the entrance of the cell in the G0G1-phase of the cell cycle on the increase of the productivity, an "on-off" mechanism should be designed where hCAII expression could be regulated during the different cultivation phases, e.g. by the use of an inducible promoter.

The following examples, sequence listing and figures are provided to aid the understanding of the present invention, the true scope of which is set forth in the appended claims. It is understood that modifications can be made in the procedures set forth without departing from the spirit of the invention.

DESCRIPTION OF THE SEQUENCE LISTING

SEQ ID NO: 01 nucleic acid encoding human carbonic anhydrase II
SEQ ID NO: 02 amino acid sequence of human carbonic anhydrase II
SEQ ID NO: 03 amino acid sequence of human carbonic anhydrase II S2A variant
SEQ ID NO: 04 primer
SEQ ID NO: 05 primer

DESCRIPTION OF THE FIGURES

FIG. 3 (A) Glucose and Lactate concentrations; (B) Cell specific Glucose consumption and Lactate production rates.

FIG. 4 (A) Ammonium concentrations; (B) Cell specific Ammonium production rate.

FIG. 5 (A) Normalized product concentration; (B) Cell specific productivity.

FIG. 6 Effects of hCAII expression and ethoxyzolamide on pHi of the Clone E11 and control cell line after acid-load. (A) Intracellular pH recovery after acid-load; (B) Carbon dioxide concentration during the acid load experiment.

FIG. 8 Effects of hCAII expression and ethoxyzolamide on pHi of the Clone E11 and control cell line after acid-load. (A) Initial pHi recovery after acid-load; (B) Comparison of the initial pHi recovery rates.

FIG. 15 Immunoblot of hCAII in cell lines stably transfected with hCAII gene and in non transfected cells. (A) Immunoblot of samples from the $CO_2$ profile cultivation. (B) Immunoblot of samples from the 5% $CO_2$ controlled cultivations. The numbers indicate cultivation days. Positive Control (PC): carbonic anhydrase isozyme II from human erythrocytes (Sigma-Aldrich); Protein marker (M): See-Bluer Plus2 pre-stained standard (Invitrogen).

EXAMPLES

Molecular Biological Methods

Figure 1:
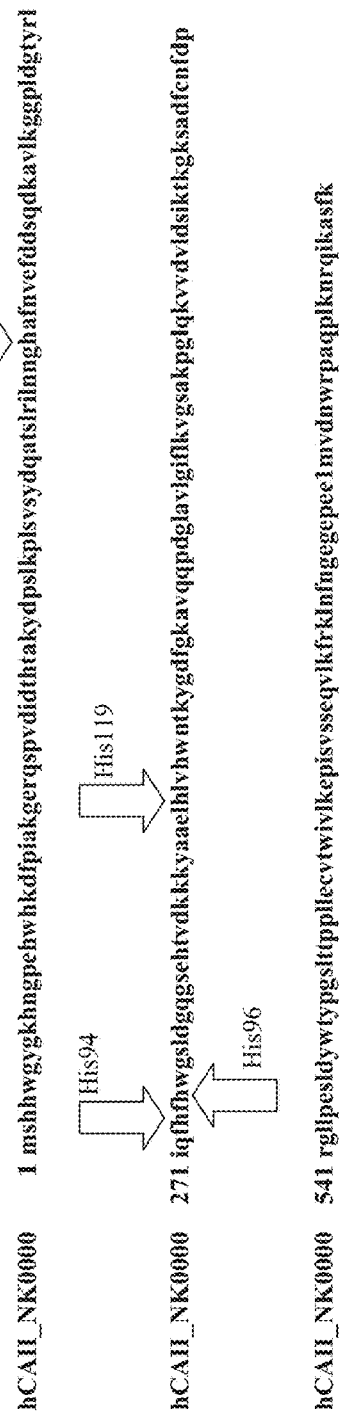
FIG. 1 Protein global alignment for hCAII gene. Encoded sequence of Data Bank NCBI (Ref. Nr.: NM000067). The active site of carbonic anhydrase formed by His64, His94, His96 and His119 is marked by arrows.
Figure 2:
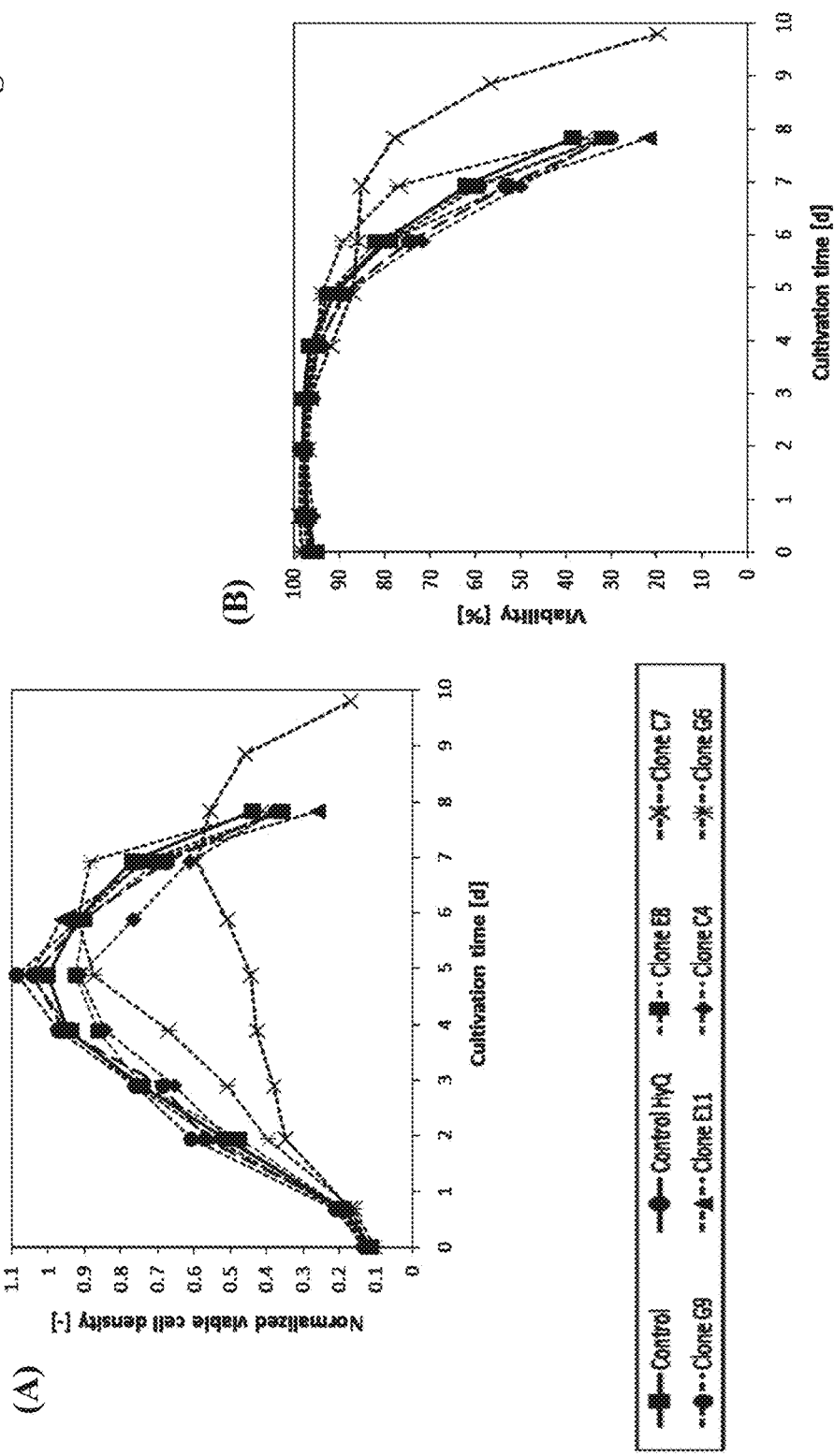
FIG. 2 Batch cultures of clones and controls in 250 ml shaker flasks with 90 ml working volume. (A) Normalized viable cell density; (B) Viability; (C) Normalized mean specific growth rate.
Figure 2:
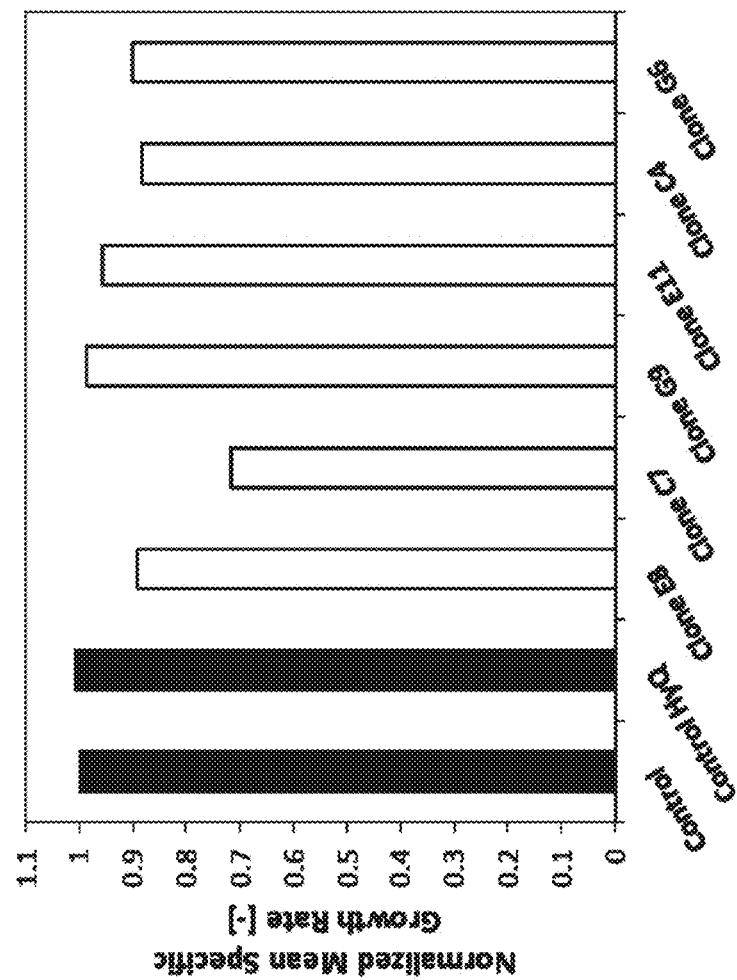
Figure 7:
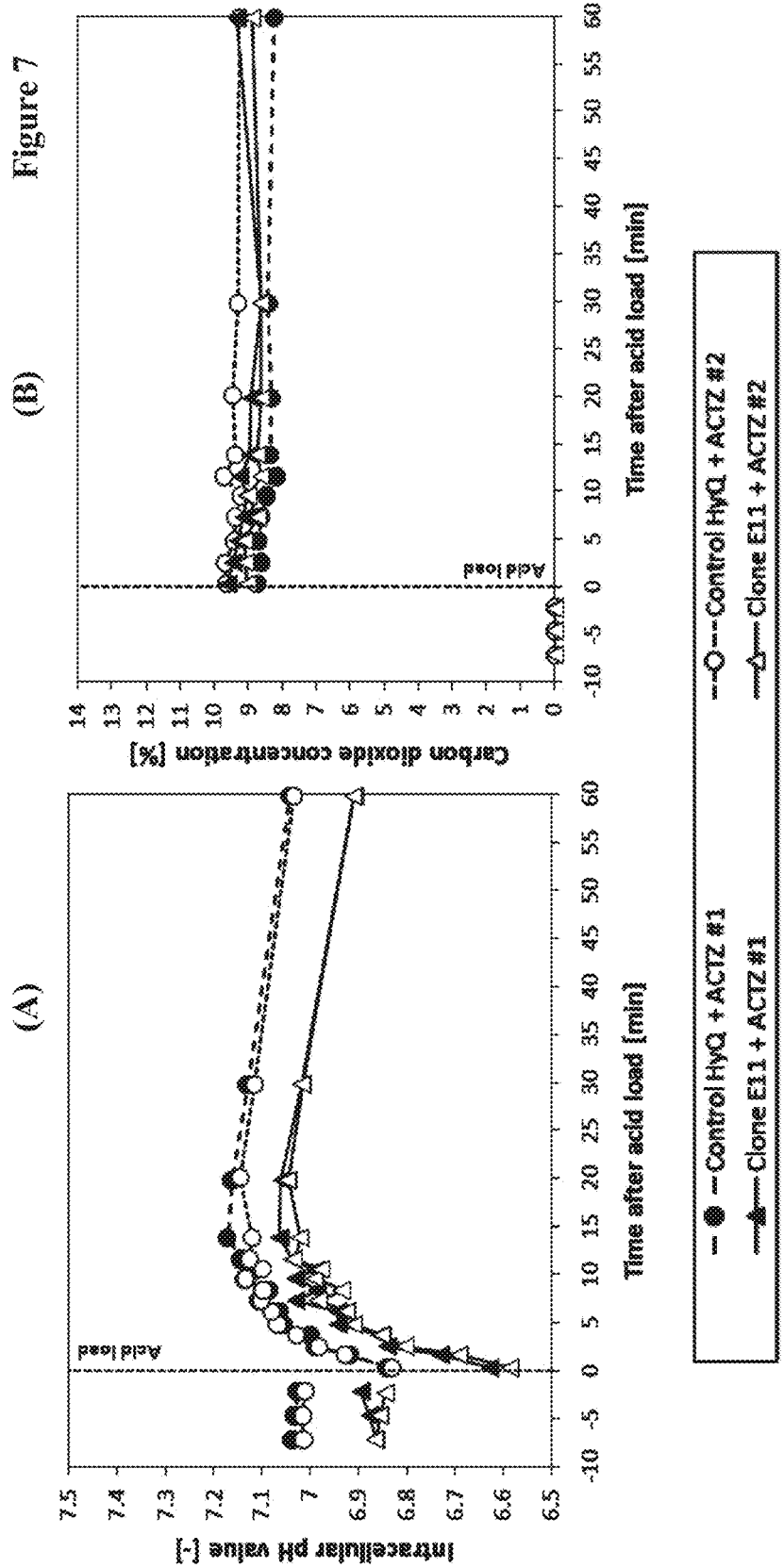
FIG. 7 Effects of hCAII expression and ethoxyzolamide on pHi of the Clone E11 and control cell line after acid-load. (A) Intracellular pH recovery after acid load in the presence of 100 μM ethoxyzolamide; (B) Carbon dioxide concentration during the acid load experiment in the presence of 100 μM ethoxyzolamide.
Figure 9:
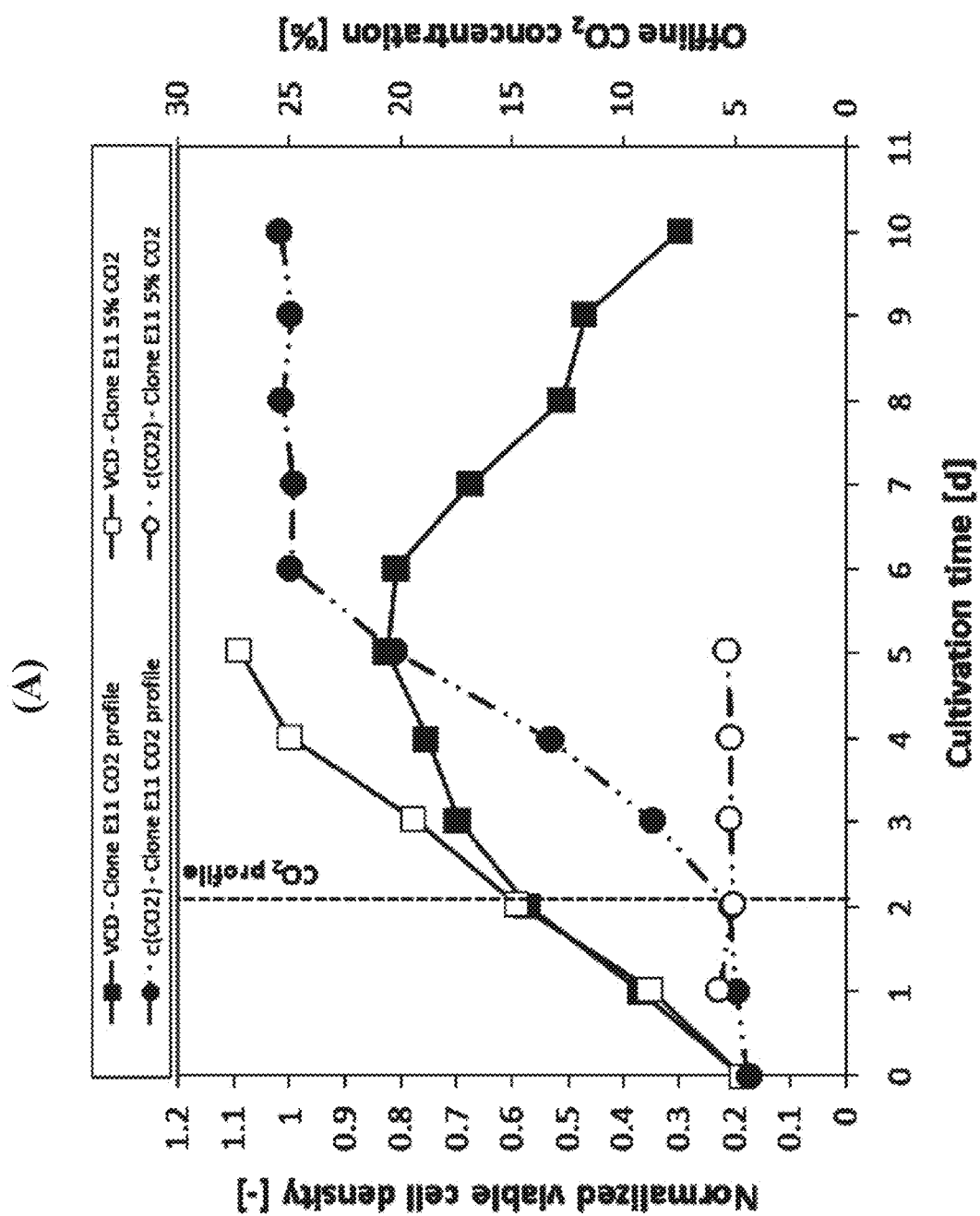
FIG. 9 Batch cultivations of the hCAII-expressing cell line E11 in bioreactor with 1.5 l working volume. (A) Viable cell density and $CO_2$ profiles. (B) Viability, specific growth rate and osmolality.
Figure 9:
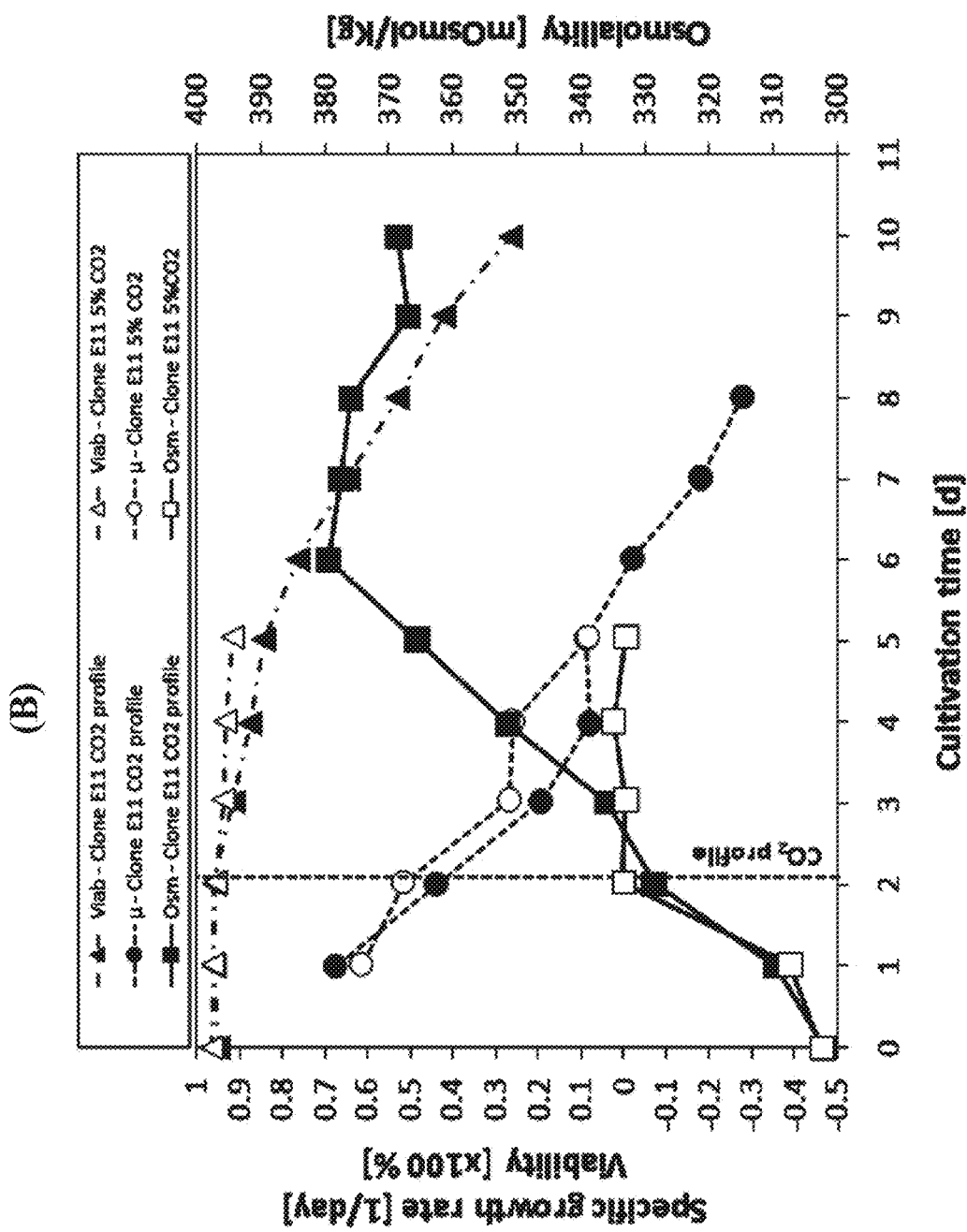
Figure 10:
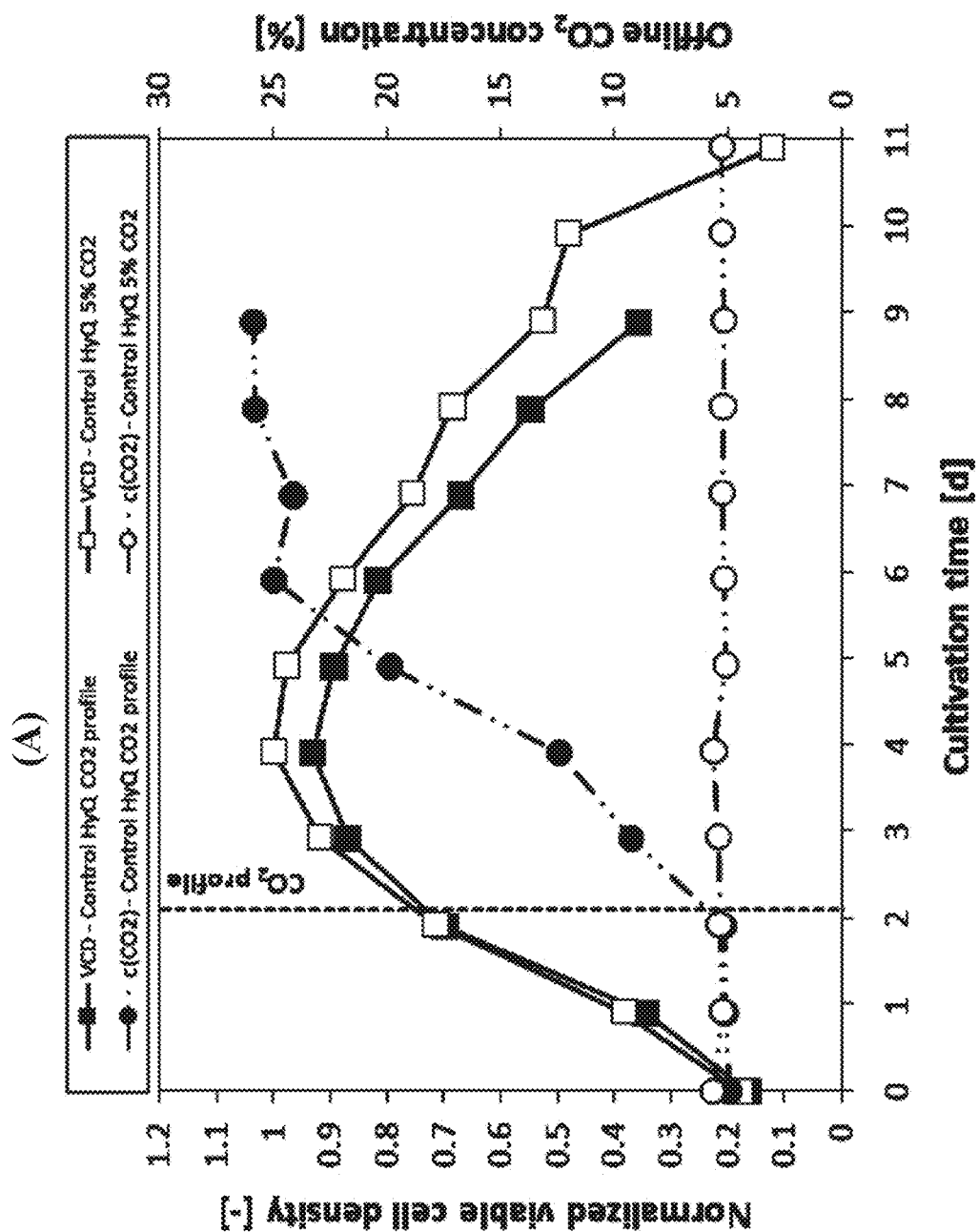
FIG. 10 Batch cultivations of the Control HyQ cell line in bioreactor with 1.5 l working volume. (A) Viable cell density and $CO_2$ profiles. (B) Viability, specific growth rate and osmolality.
Figure 10:
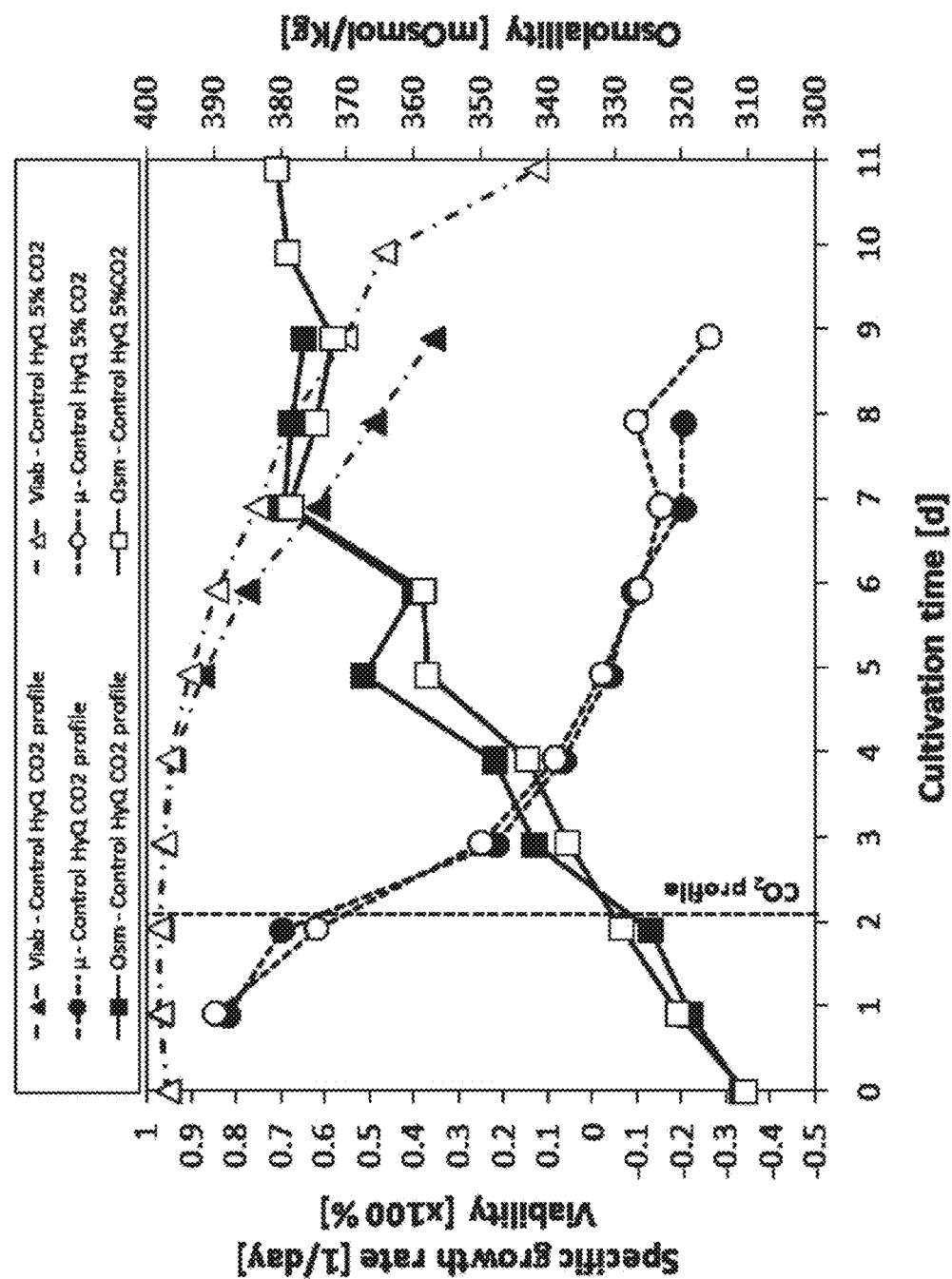
Figure 11:
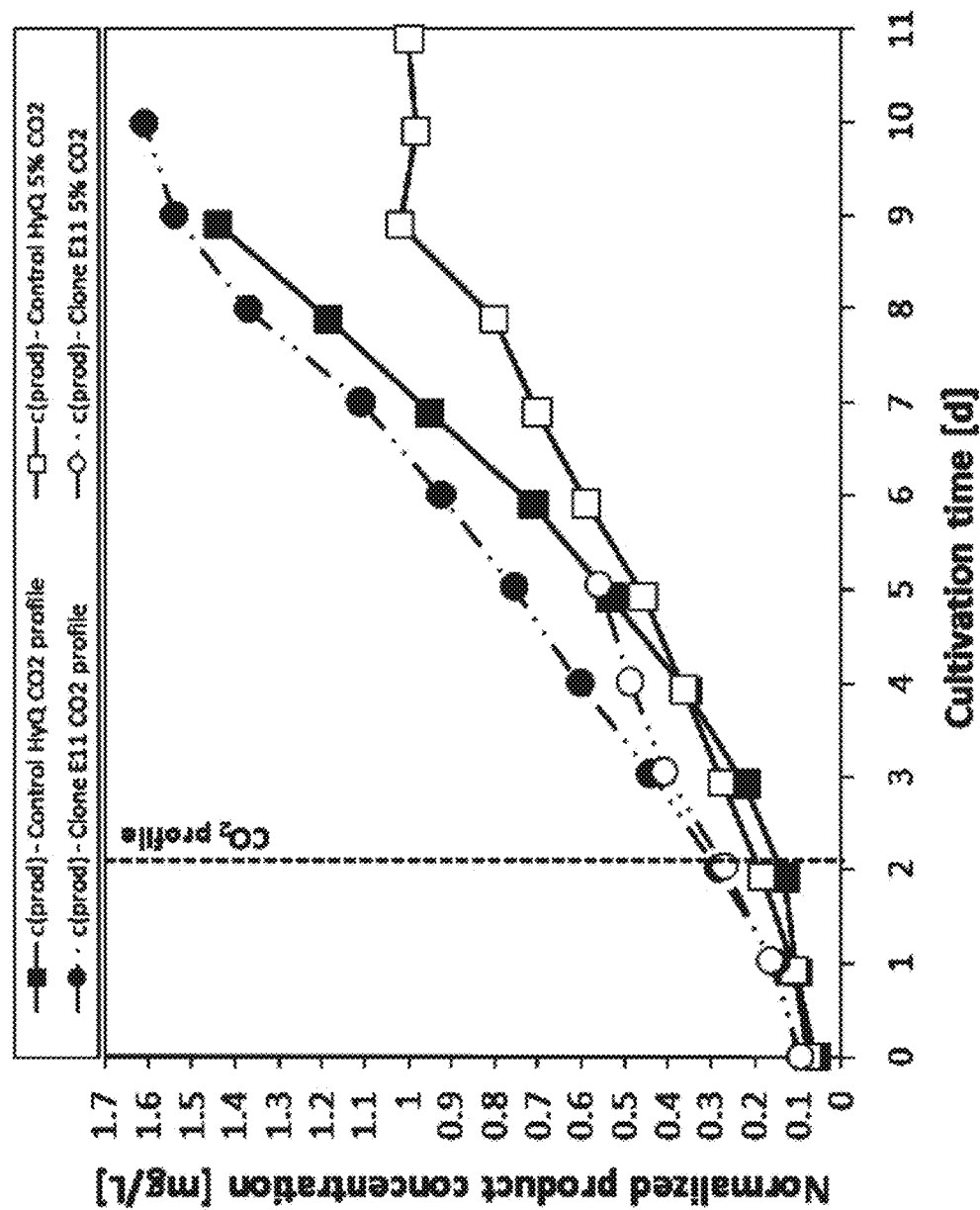
FIG. 11 (A) Normalized product formation; (B) Product cell specific production rate.
Figure 11:
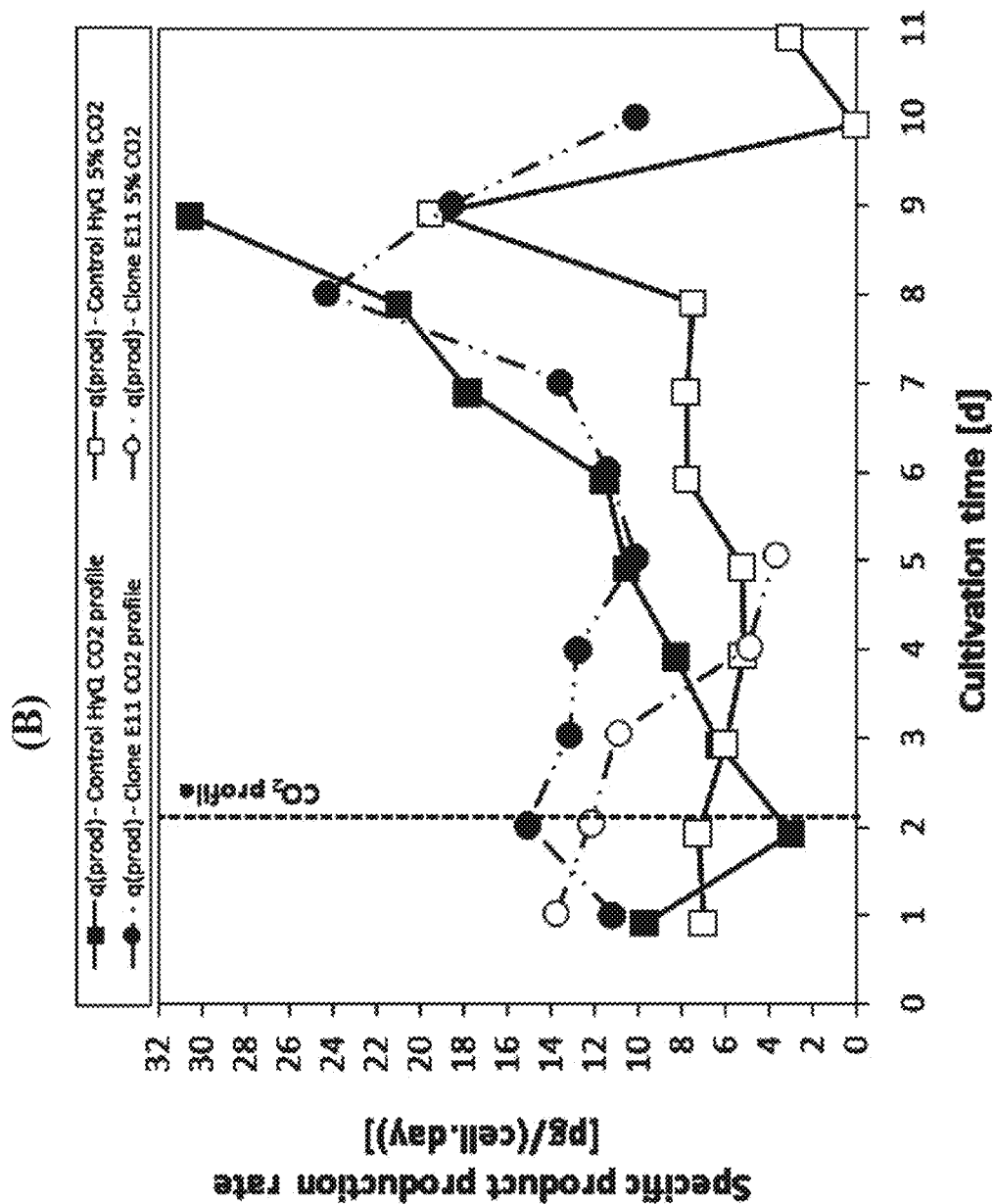
Figure 12:
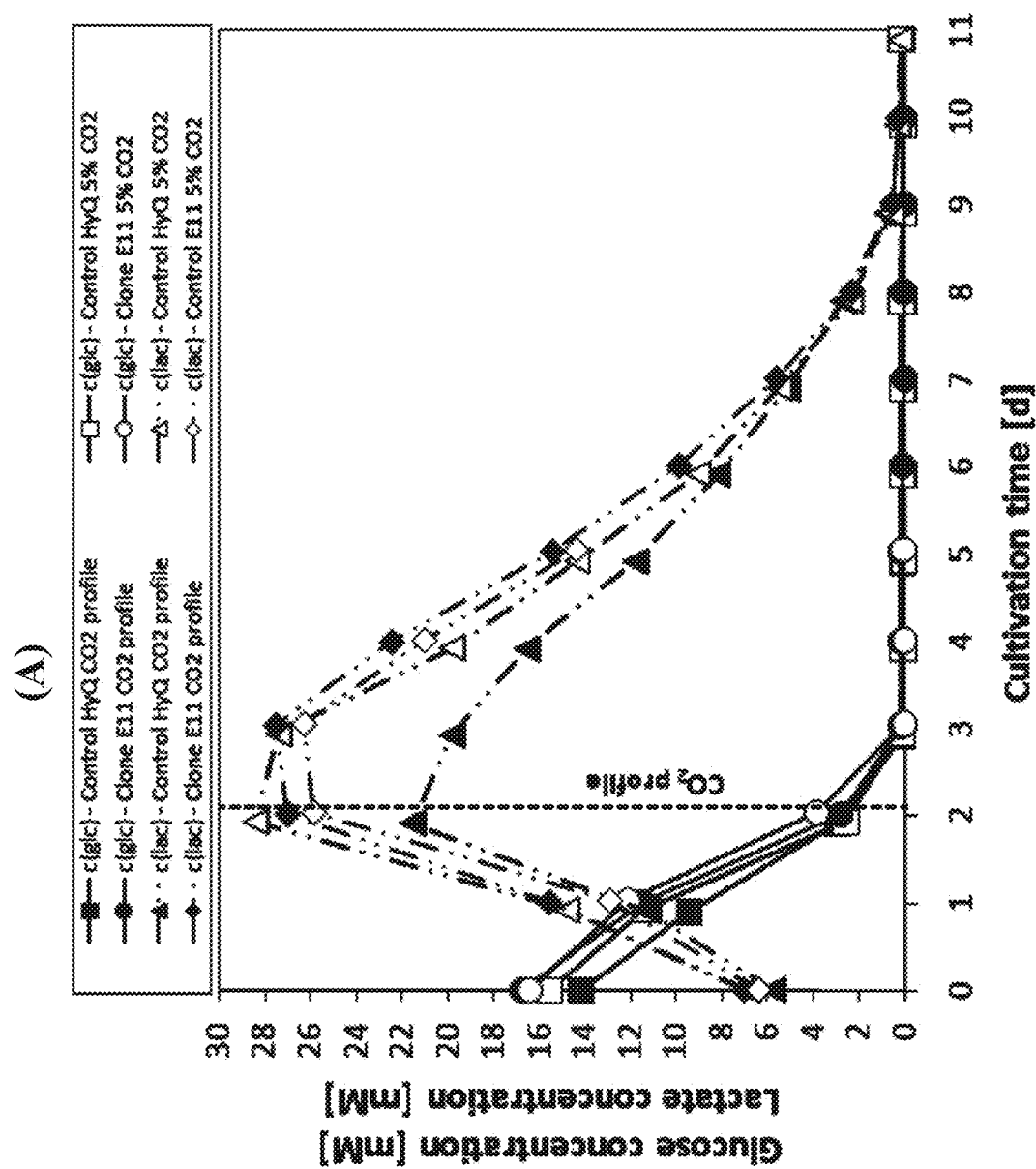
FIG. 12 (A) Glucose and Lactate concentrations; (B) Cell specific glucose consumption and lactate production rates; (C) Ammonium concentrations; (D) Cell specific ammonium production rates.
Figure 12:
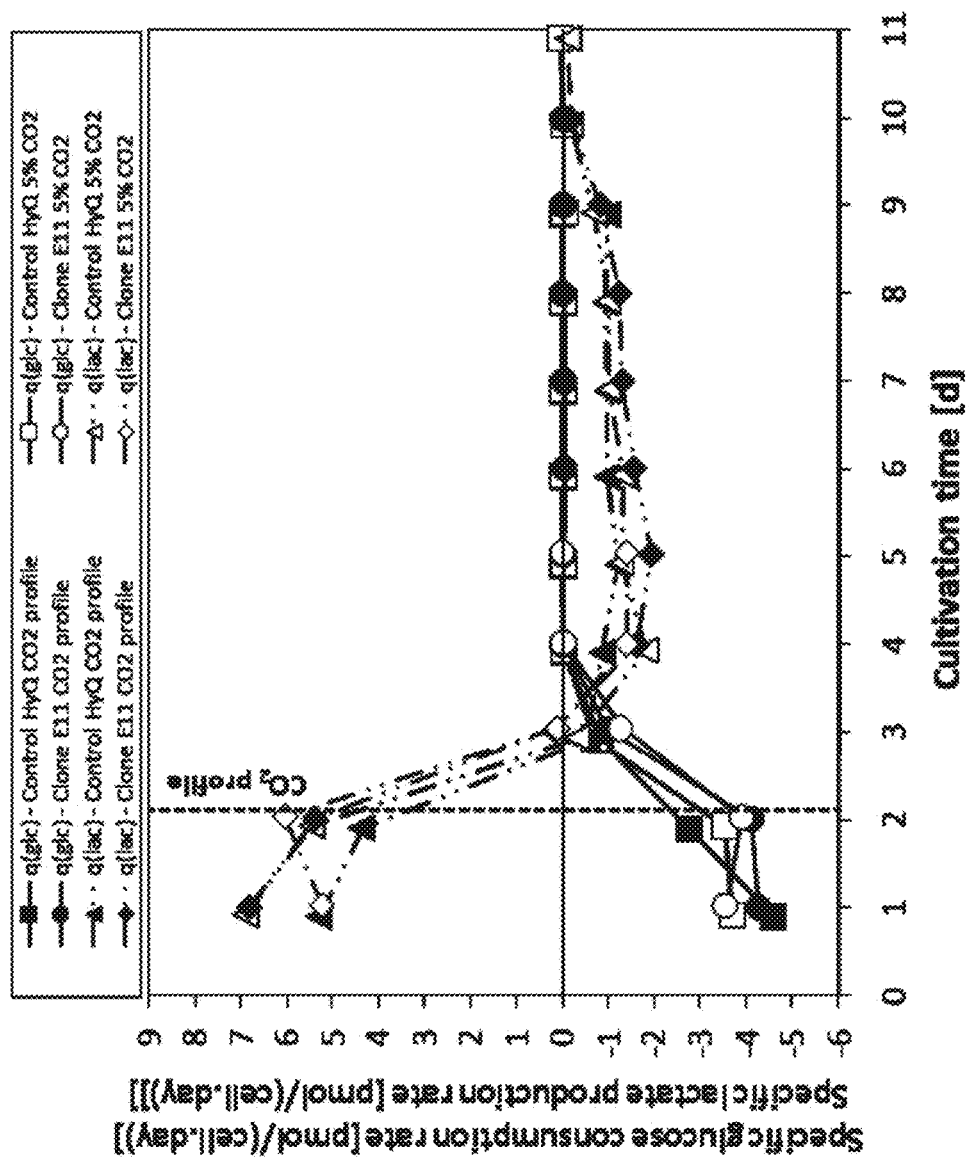
Figure 12:
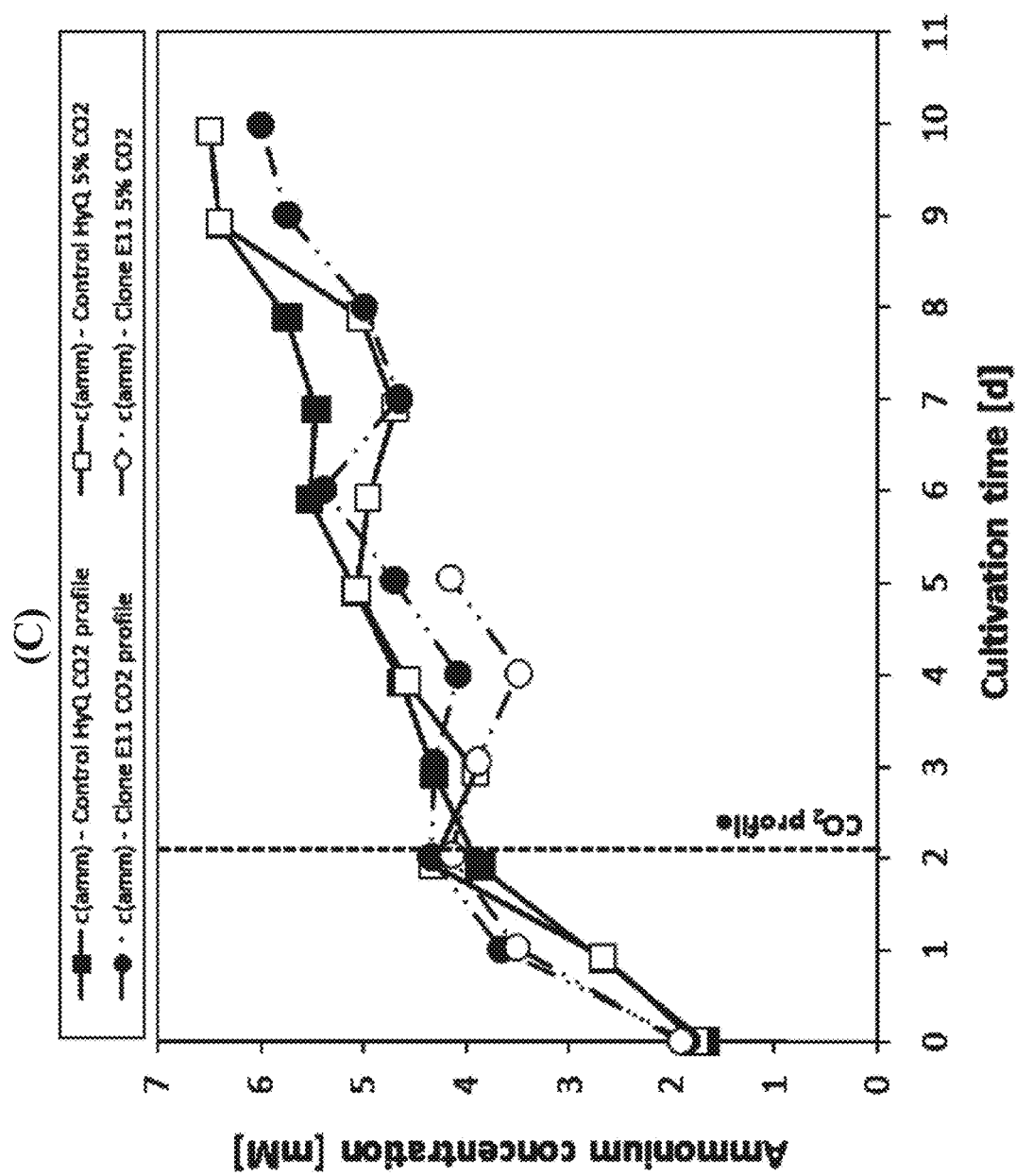
Figure 12:
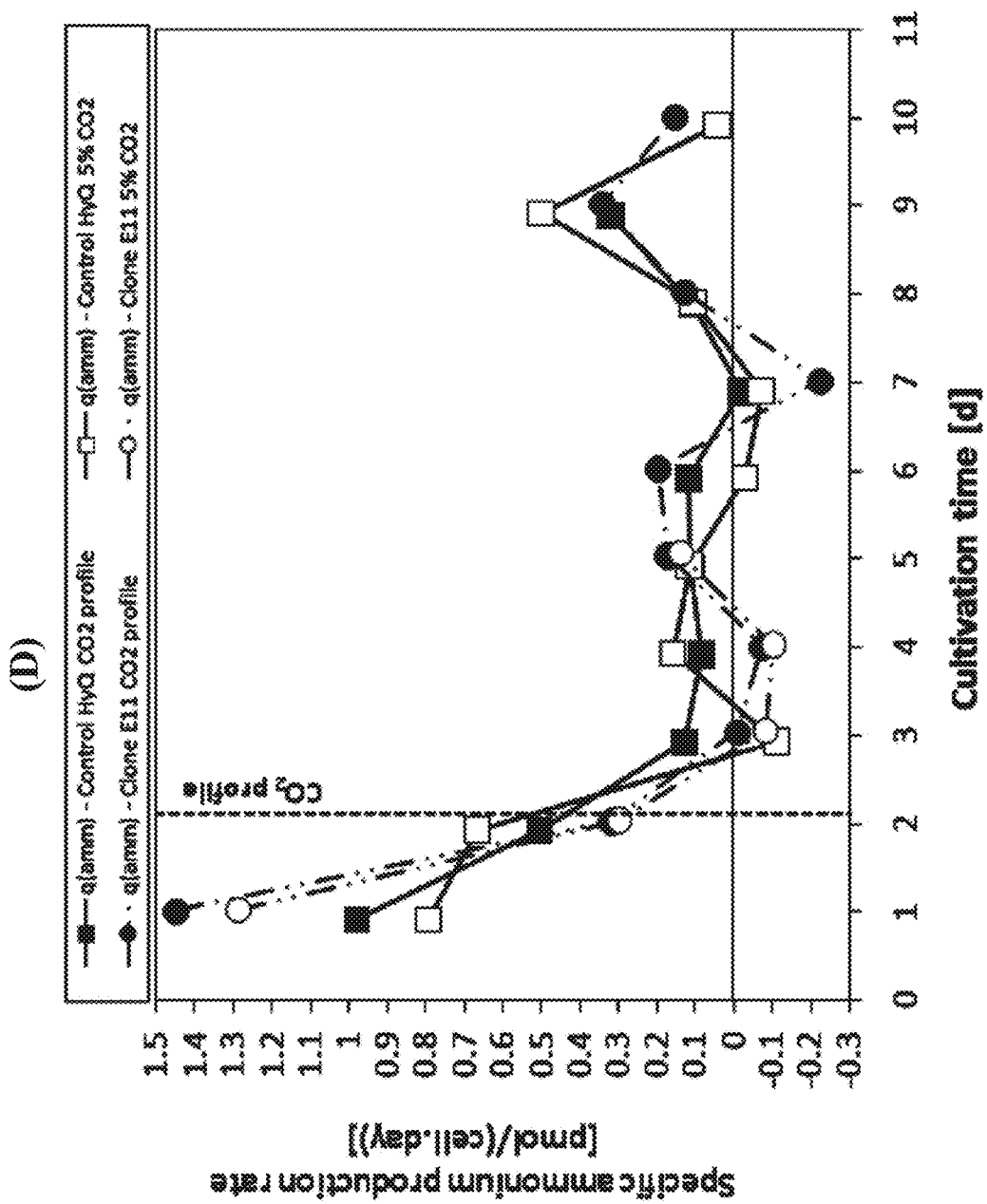
Figure 13:
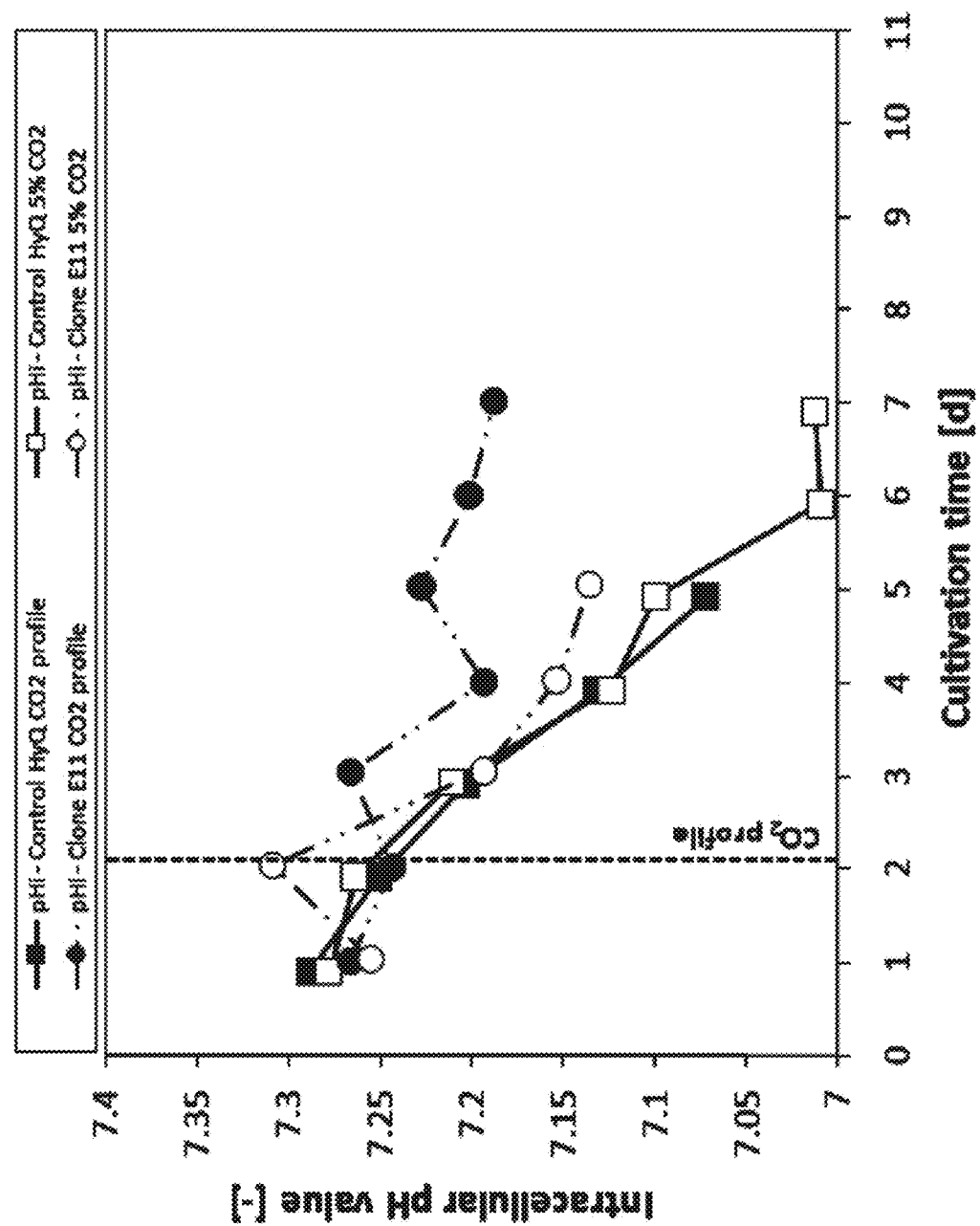
FIG. 13 Course of intracellular pH value for a cultivation with extracellular pH value controlled to pH 7.2.
Figure 14:
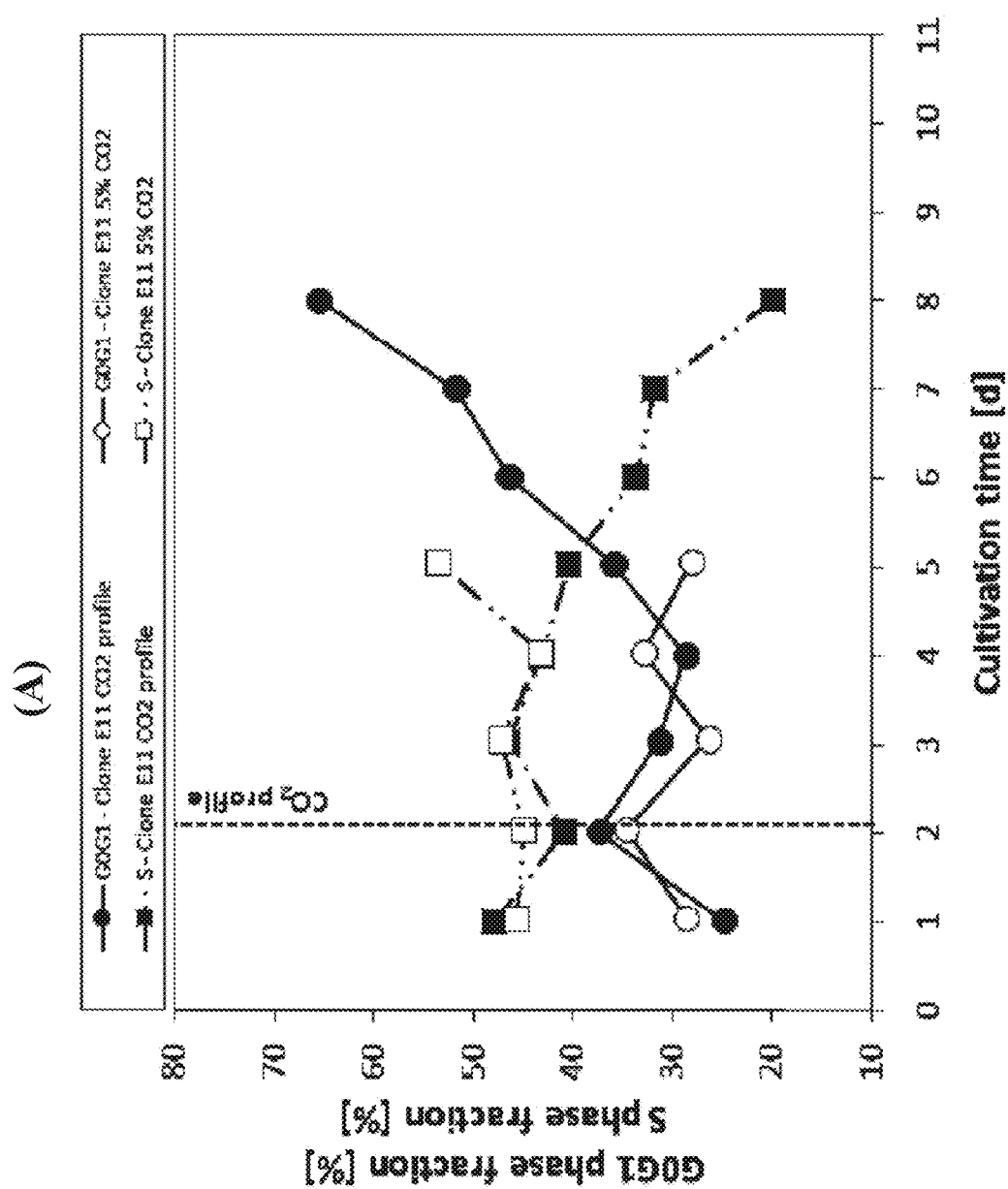
FIG. 14 Changes in the fraction of cells in G0G1 and S phases during batch cultures of clone E11 (A) and Control HyQ (B) at controlled 5% $CO_2$ and $CO_2$ profile.
Figure 14:
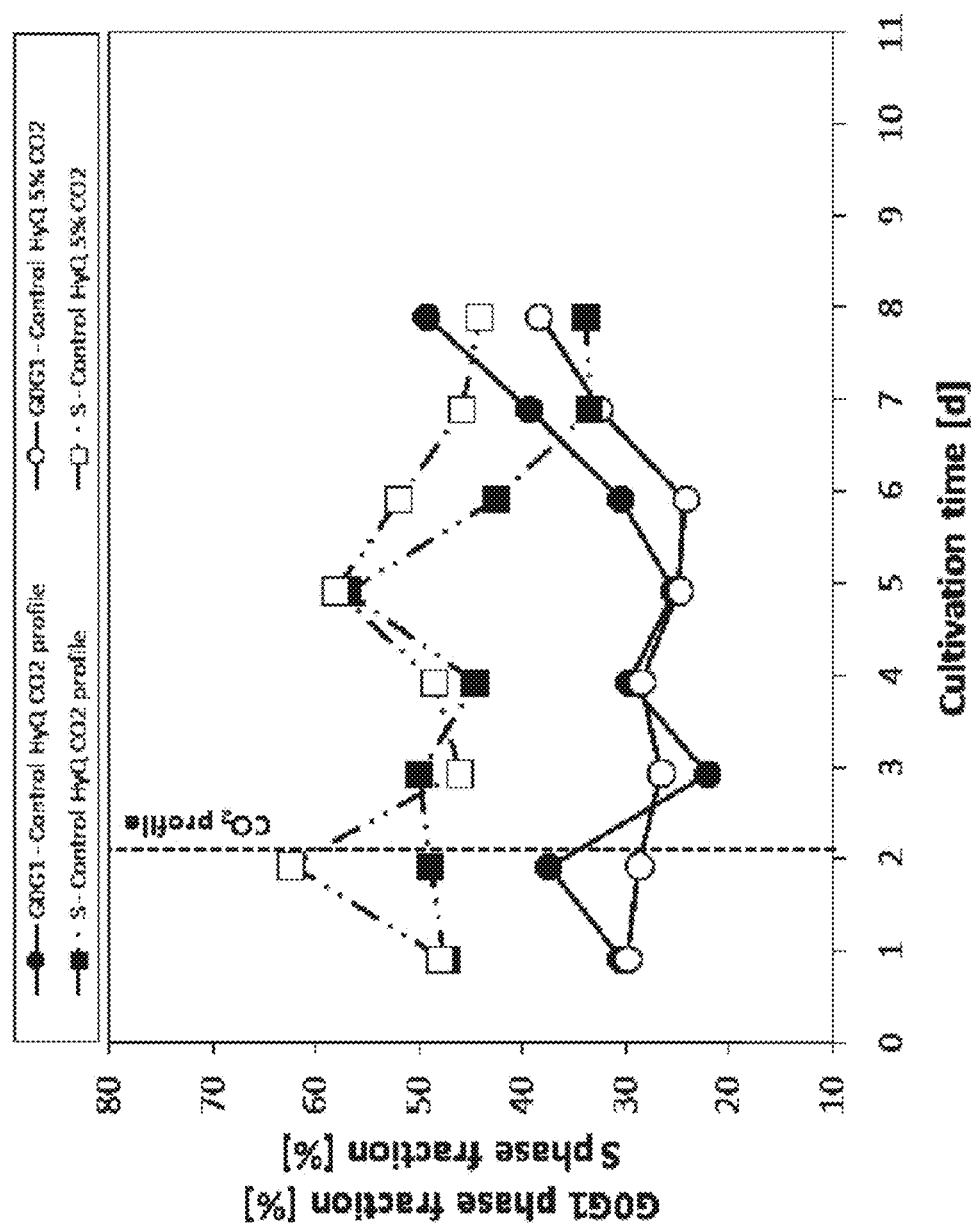
Figure 16:
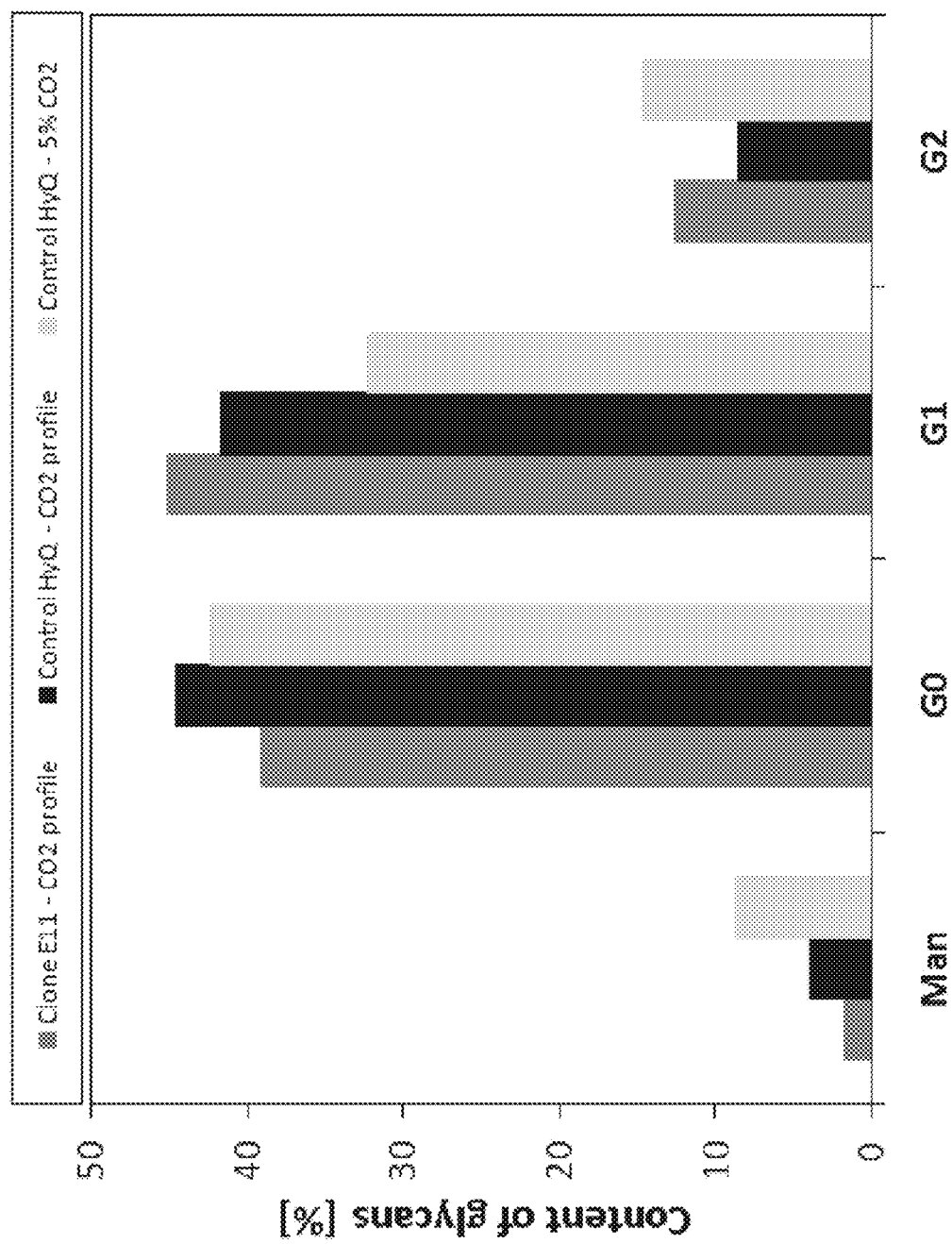
FIG. 16 Comparison of the glycosylation profile of the recombinant protein produced by the cells under increased $CO_2$ profile with the one produced at controlled 5% $CO_2$.
Figure 17:
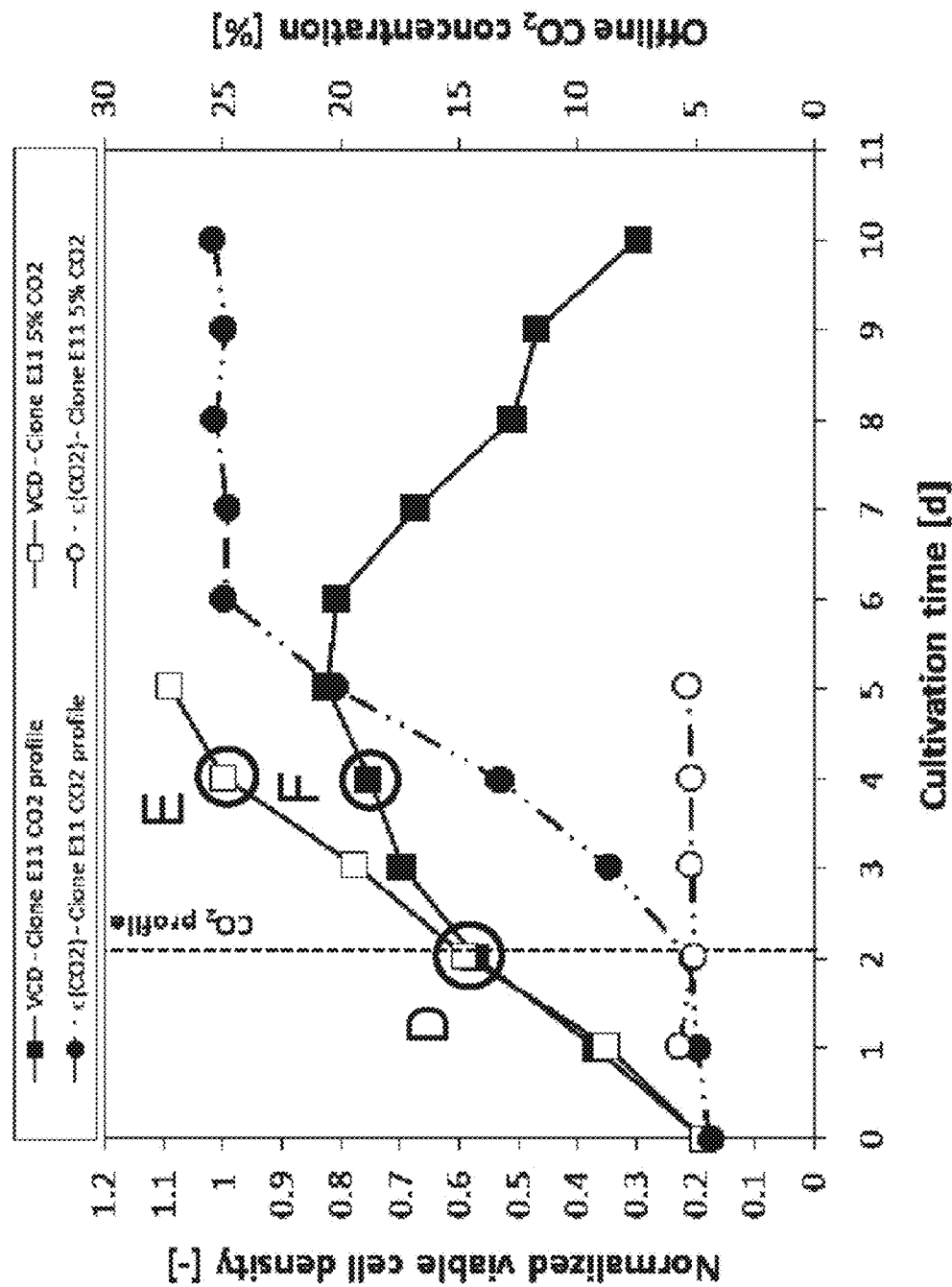
FIG. 17 Sampling of the batch cultivations for proteomic analysis. (A) Clone E11 (B) Control HyQ. Samples A and D at day 2 (constant 5% $CO_2$), samples B and E at day 4 (constant 5% $CO_2$), samples C and F at day 4 (13% $CO_2$).
Figure 17:
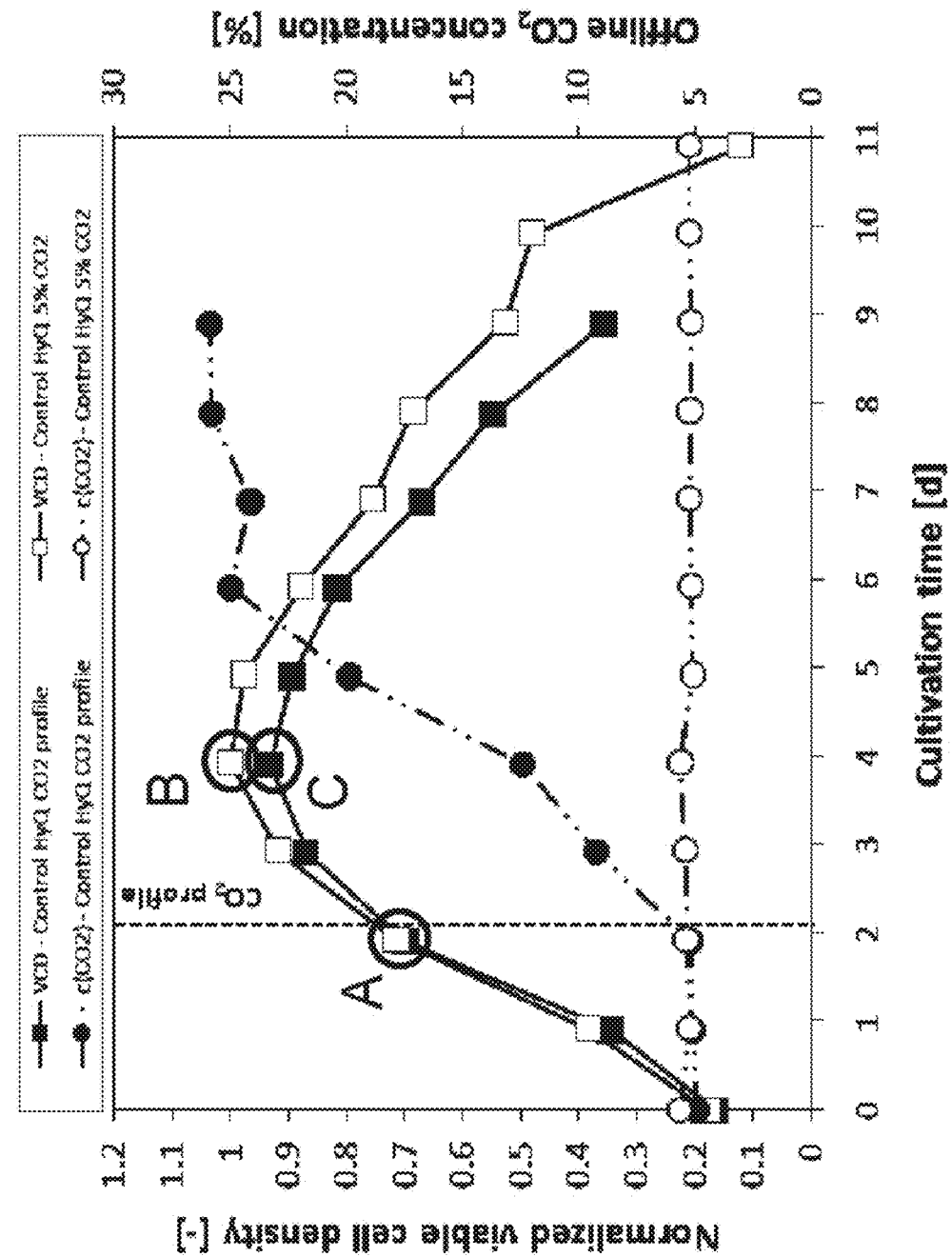

To prepare clones of CHO cells, a three step approach is taken. First, the gene of interest (GOI) is cloned into an appropriate mammalian expression vector. Second, the resulting plasmid is prepared in E. coli, and finally, the construct-bearing plasmid is introduced into the CHO cells, where the desired DNA is incorporated in the genome.

Vectors

The mammalian expression vector for hCAII gene (NCBI Ref. Seq.: NM000067) has a size of 4807 bp and it confers ampicillin resistance (Ampr) in E. coli. The pJRC36 vector construction is described by STERLING, D. AND CASEY, J. R., Biochem. J. 344 (1999) 221-229.

Plasmid DNA Restriction

For the preparation of linear DNA for nucleofection, 20 μg of DNA were incubated in a reaction mixture with a total volume of 200 μl containing 100 units of the restriction enzyme ApaLI. The restriction occurred by incubation for 4 h at 37° C. Afterwards, a 100 ng sample was analyzed by gel electrophoresis. After confirmation of DNA linearization, additional purification steps with Phenol-Chloroform extraction and ethanol precipitation were done in order to remove enzyme and salts from the DNA.

Primer Design

Primers for sequencing purposes were chosen to have a length of 20 to 22 nucleotides and a GC content of about 50%. The melting temperature of a primer is defined as the temperature at which 50% of the double strand DNA (ds-DNA) has denatured. The annealing temperature (TA) is the temperature at which the primer anneals to a single-stranded DNA template and is considered as 5° C. lower than the TM. The melting temperature was between 60° C. and 80° C. and did not differ more than 5° C. between primer pairs. Primers were designed with no intra-primer homology beyond 3 base pairs. It was also considered the inclusion of more than one G or C residue at 3' end of primers to ensure correct binding.

All primers were designed with the program Clone Manager Suite 7 (Sci-Ed Software). The following Table gives an overview of the resulting primers used for sequencing of hCAII gene in the vector. These primers were purchase from Invitrogen, dissolved in LAL-H2O to a final concentration of 10 pmol/μl and stored at −20° C. The orientation of a primer is indicated by "+" for a sense primer and "−" for an antisense primer. The location of the primers hybridization region is also indicated. The melting temperatures (TM) were calculated with the program Clone Manager Suite 7 (Sci-Ed Software).

TABLE

| Primer | +/− | Location in phCAII-ZsGreen1 | Sequence (5'→3') | $T_M$ [° C.] | |
|---|---|---|---|---|---|
| PR07 | + | 569 | GGTTTAGTGAACCGTCAGATCC | 60 | SEQ ID NO: 04 |
| PR08 | + | 1251 | AAAGGGCAAGAGTGCTGACTTC | 62 | SEQ ID NO: 05 |

Sequencing

The sequencing of hCAII was performed at the Center for Biotechnology (CeBiTec, Bielefeld, Germany).

Nucleofection of Mammalian Cells

Nucleofection was performed with linearized DNA. Nucleofection of CHO cells was performed with the Nucleofector™ II according to the protocol provided by the manufacturer (Amaxa Biosystems, Cologne, Germany). In short, $5 \times 10^6$ cells were harvested, gently mixed in 100 µl of Cell Line Nucleofector® Solution V and 4 µg of linear DNA and transferred into a 0.1 cm gap cuvette. Immediately after, the cells were pulsed with the program U-024 of the Nucleofector™ II (Amaxa Biosystems), then pipetted into a 15 ml falcon tube containing 10 ml pre-warmed HyQ medium and spun down at 200×g for 10 min. at RT. The pellet was resuspended in 5 ml pre-warmed HyQ medium and transferred into a T-25 flask. After 24 h incubation at 37° C. and 5% $CO_2$, the cells were assayed for both viability and expression (transfection efficiency). After 48 h, the clone mixture was submitted to a limited dilution for single clone isolation.

Mammalian Cells

A Chinese Hamster Ovary (CHO) cell line producing an antibody was used. The cell line was created by transfecting the dihydrofolate reductase (DHFR) negative parent CHO cell line with a recombinant vector containing genes for both a DHFR and the antibody. The transfected genes were amplified by the DHFR inhibitor and methotrexate (MTX). A high producer was selected and cloned. The final cell line also contains resistance against hygromycin.

Media for Cultivation of Mammalian Cells

Pre-culture medium containing methotrexate was used for inoculum preparation and the main cultivations were performed in production medium. The different components were dissolved in MilliQ-$H_2O$. The pH value of the medium was adjusted to pH 7.2 with 25% (v/v) HCl. After sterile filtration (0.2 µm) and supplementing, the medium was stored at 4° C. A sterile test was performed for 48 h at 37° C. and the medium was used no longer than 4 weeks after production. The commercial available HyQ® SFM4CHO™-Utility medium (Hyclone) was used as outgrowth medium after nucleofection.

Monod Kinetic

Following are the formulas for calculating the specific rates. Since for this type of cultivation strategy there is no flow in or out from the bioreactor the volume is considered constant (Equation 10.2). The cell concentration (X) of a growing culture is changing with time (t) according to Equation 10.2, which after integration and taking the logarithm originates the equation for calculating the specific growth rate (µ). The medium culture substrates are consumed as result from cell growth. They are used by cells for the maintenance of metabolic processes and for product formation. The specific substrate consumption (qS) and product formation rates (qP) are calculated by Equations 10.4 and 10.5, respectively, with the mean cell concentration (Xm) calculated according to Equation 10.6.

$$\frac{dV_L}{dt} = 0 \quad (10.2)$$

$$\frac{dX}{dt} = \mu \cdot X \Rightarrow \mu = \frac{\ln(X_{i+1} - X_i)}{t_{i+1} - t_i} \quad (10.3)$$

$$\frac{dS}{dt} = q_S \cdot X \Rightarrow q_S = \frac{1}{X_m} \cdot \frac{S_{i+1} - S_i}{t_{i+1} - t_i} \quad (10.4)$$

$$\frac{dP}{dt} = q_P \cdot X \Rightarrow q_P = \frac{1}{X_m} \frac{P_{i+1} - P_i}{t_{i+1} - t_i} \quad (10.5)$$

$$\text{with } X_m \frac{X_{i+1} - X_i}{2} \quad (10.6)$$

$V_L$ volume of liquid in bioreactor [L]

$X$ cells concentration $\left[\frac{\text{cells}}{\text{mL}}\right]$ $\mu$ specific growth rate $\left[\frac{1}{\mu d}\right]$ $S$ substrate concentration $\left[\frac{\text{mmol}}{\mu L}\right]$ $q_S$ specific substrate consumption rate $\left[\frac{\text{pmol}}{\text{cell} \cdot d}\right]$ $P$ product concentration $\left[\frac{\text{mmol}}{\mu L}\right]$ $q_P$ specific product production rate $\left[\frac{\text{pmol}}{\text{cell} \cdot d}\right]$ $t$ cultivation time [d]

$X_m$ mean cell concentration $\left[\frac{\text{cells}}{\text{mL}}\right]$

Establishing of Working Cell Bank (WCB)

A working cell bank (WCB) for the original cell line (Control) was setup to ensure sufficient cell resources for all experiments. Therefore, cell density and viability were measured for an exponential growing culture. Afterwards, cells were harvested and cell pellet was resuspended in a defined volume of chilled pre-culture medium with 5% DMSO (dimethyl sulfoxide) in such a way, that the final cell concentration was $1 \times 10^7$ cells/ml. Four milliliters of this cell suspension were aliquoted in cold 4.5 ml nominal volume cryovials (Nunc®) and cell suspension was frozen with the IceCube 1800 (SY-LAB GmbH) according to manufacturer's instructions (Instructions Manual for Ice Cube 1800, V4.01 from Aug. 1, 2001, SY-LAB). The cryovials were transferred to the gas phase of the liquid nitrogen for long time preservation.

The WCB of the hCAII-clones or control cell line in HyQ medium, were done either with HyQ freezing medium or with pre-culture freezing medium, both containing 5% DMSO. Therefore, $1 \times 10^7$ cells/vial were frozen overnight at −80° C. in the 5100 Cryo 1_C Freezing Container (Nalgene) which induces a cooling rate of −1° C./min. Afterwards, the cryovials were transferred to the gas phase of the liquid nitrogen.

Cultivation

Back-up or inoculum cultures and parallel test batches were carried out in disposable cultivation systems, such as bioreactor tubes and shaking flasks. 50 ml conical polypropylene bioreactor tubes (TPP) and different nominal volume (125 ml, 250 ml and 500 ml) polycarbonate Erlenmeyer flasks (Corning) were used. Both were equipped with polyethylene plug seal caps with integrated 0.22 µm hydrophobic membrane to maintain sterility and facilitate gas exchange. For bioreactor tubes the working volume ranged between 10 ml and 20 ml and for shaking flasks between 40% and 60% of the nominal volume. The cultivations were performed in an incubator (Mytron) at 37° C., 5% $CO_2$ and 80% humidity. Agitation was achieved by orbital shaking at 125 rpm (Innova 2300, New Brunswick Scientific) or 185 rpm (ES-X, Kuhner), and 0° inclination angle for bioreactor tubes.

Back-Up Cultures

One WCB cryovial of the control cell line was quickly thaw in a 37° C. water bath and the cell suspension was mixed with 10 ml pre-culture medium (RT). After centrifugation (200×g, 10 min) to remove the DMSO, the pellet was resuspended in 10 ml pre-culture medium at room temperature. After cell density and viability determination, a 125 ml shaking flask was inoculated at $5 \times 10^5$ cells/ml.

Clones or control cell line in HyQ medium thawing procedure was similar to the one described for the control cell line, except that after pellet resuspension in 15 ml fresh pre-culture medium, cells were cultured in 50 ml bioreactor tubes at 185 rpm (ES-X, Kuhner), and 0° inclination angle. After 2 days, cells were transferred to a 125 ml shaking flask.

Sub-culturing was performed every 3 days from an initial cell density of $4 \times 10^5$ cells/ml for control cell line or $6 \times 10^5$ cells/ml for the hCAII over-expressing clones and control cell line in HyQ medium. Back-up cultures were run for 1 month at most.

Parallel Batches

Cells were seeded at $6 \times 10^5$ cells/ml and cultivated in pre-culture medium in 250 ml shaking flasks with 90 ml working volume at 185 rpm. After a 2 day adaptation phase, the main culture was inoculated in production medium. Samples of 2 ml were taken daily for cell density analysis, 1 ml was centrifuged (200×g) for 10 min. at RT. The ammonium concentration in the cell free-sample was measured and the remaining supernatant was aliquoted and stored at −20° C. for glucose, lactate, and product analysis. The cultivations were aborted when viability dropped below 40%. The cells were harvested and 40 ml of the cell-free supernatant were stored at −20° C.

Clone Screening

For the generation of clonal cell lines, the clone pool was diluted in such a way that single cells were obtained by cultivation in 96-well plates under selective cultivation conditions (selective pressure). Forty eight hours after nucleofection, cell density and viability were checked. The clone pool was spun down and the pellet resuspended to a concentration of $2 \times 10^3$ viable cells/ml in selective medium (HyQ medium with 5% FBS and 400 µg/ml G418). Further dilutions were performed in order to inoculate 96-well plates (flat-bottom, Nunclon™, Nunc) with 100, 20, 10 and 5 viable cells in each well with 150 µl selective medium. The plates were incubated at 37° C. and 5% $CO_2$ for formation of colonies. After 7 days, 50 µl of selective medium was added to the wells. Between 8 and 12 days and selection conditions plates were checked regularly and wells containing single colonies were marked. Seventeen days after the selection procedure had started, single colonies were trypsinized by first aspirating medium and after a washing step with PBS, the cells were incubated for 5 min at 37° C. with 50 µl 1× trypsin (Invitrogen). Afterwards, trypsinized cells were transferred to 24-well plates for further cultivation without selective pressure. When the colony size permitted it, the clones were further cultivated in 35 mm dishes. Once 90% confluency was reached, part of the cells were harvested and prepared for hCAII-expression analysis, the other part was further expanded in t-25 flasks, t-75 flasks, bioreactor tubes and, finally in 125 ml Erlenmeyer flasks. In the middle of the exponential growth phase cells were split, half of which were cryopreserved in HyQ medium with 5% DMSO. The other half was centrifuged down, resuspended in pre-culture medium and further cultivated until middle exponential phase. Cryopreservations were performed in pre-culture medium with 5% DMSO. The control cell line was cultivated throughout the screening process in HyQ medium and cryopreserved accordingly.

Bioreactor Cultivations

Batch cultivations were performed in the multi-bioreactor system Biostat B-DCU (Sartorius AG) with 1.5 l working volume. The on-line monitoring of the process parameters was performed with in-place sensors, such as: pH electrode, $pO_2$ electrode, $pCO_2$ electrode and temperature electrode. The process parameters were controlled through the DCU local controller (Sartorius AG). The pH value was automatically adjusted to 7.20±0.01 by addition of 1 M NaOH or 1 M HCl. Bioreactor gassing was performed with a sterile gas mix (0.2µ, inlet sterile filter) by a ring sparger, immersed in the culture liquid under the impeller. Exhaust gas was cooled down by an exhaust gas cooler and left the bioreactor through an outlet sterile filter. The bioreactor was equipped with two 4-bladed Rushton type impellers. For $pO_2$ controlling, a cascade with gas flow rate (GAFR) and agitation (STIR) was used in the ratio mode with total flow rate of 60 ml. A mixed gas containing air and nitrogen was used to maintain the dissolved oxygen concentration at 30.0±0.1% air saturation. When the air flow rate reached the maximum value, the agitation (second cascade parameter), was controlled according to cells oxygen demands. The initial agitation value was 80 rpm. An additional mix of $CO_2$ and $N_2$ was used to control the $pCO_2$ at the desired concentrations (constant 5% $CO_2$ or continuous $CO_2$ profile from 5% to 25% $CO_2$). The bioreactor temperature was maintained at 37° C. and controlled through the jacket water temperature. To exclude osmolality differences between the $CO_2$-controlled cultivation modus, this parameter was manually compensated with addition of 1 M NaCl (equivalent to 1843 mOsmol/kg) through a calibrated peristaltic pump. To avoid formation of foam, 1% anti-foam solution was added when necessary. The reactors with the probes in place and filled with 1.5 l PBS was submitted to a pressure test. Afterwards, steam-sterilized at 121° C. for 50 min.

The inoculum for the main-culture was prepared in the bioreactor at 5% $CO_2$ and in production medium until it reached the middle exponential growth phase. The main cultures were inoculated at $6 \times 10^5$ cells/ml. For sampling, the sterile coupling system with Luer-Lock (DASGIP GmbH) was used. Samples were taken every 24 h for cell growth, productivity, cellular metabolism, cell physiology etc. For sampling, syringes with the Luer-Lock system were used together with the Luer-Lock system built up in the bioreactor. To take a representative sample of the culture, a pre-flow sample (about 5 ml sample) was taken, after which, enough volume of cell suspension was removed and directly measured in the blood gas analyzer (ca. 100 µl) for off-line analytic (pH, $pCO_2$) and for cell density determination. Part of the remaining cell suspension was used for generation of samples for cell cycle analysis ($2 \times 10^6$ cells) and hCAII expression level ($1 \times 10^6$ cells) during the cultivation, the other part was centrifuged at 200×g for 10 min. at RT. The ammonium concentration in the cell free-sample was measured and the remaining volume was aliquoted and stored at −20° C. for glucose, lactate and product analysis. For pHi measurement, about 2.5 ml cell suspension was taken. Finally, the sampling system was sterilized with 70% ethanol.

The cultivations were performed until viability decreased below 40%. At this time, the cells were sterilely harvested from the bioreactor and 40 ml supernatant were frozen for glycan analysis. The $pCO_2$, $pO_2$ and pH probes were removed and the bioreactor was filled with 0.2 M NaOH.

Inactivation was done overnight (45° C., 100 rpm). Finally the reactor was cleaned with MilliQ-H$_2$O.

Determination of Viable Cell Density and Viability

Cell densities and viability of the cultures were determined with the automated cell counting system Cedex (Cell Density Examination System, Roche Innovatis GmbH). The measurement is based on the well-established Trypan Blue dye exclusion method for determination of living and dead cells. Sample handling, staining, cell counting, image acquisition and analysis were performed automatically by the Cedex. For better accuracy, two measurements each of 1 ml were performed for each sample (30 images). The samples from disposable bioreactors experiments were diluted 1:2 with PBS before measurement.

Determination of Metabolites Glucose and Lactate

The automatic Glucose-Lactate Analyzer YSI 2700D Select was used for the measurement of these parameters in supernatant. The instrument calibrates automatically with glucose and lactate solutions of defined concentrations. A repeat determination was performed, for each of which 150 µl sample was necessary. All samples were diluted in PBS buffer in such a way that measured concentrations were below the concentrations of the standard solutions.

Determination of Ammonium

A specific and sensitive determination of ammonium is achieved by its derivatisation in the alkaline environment to fluorescent derivatives. For the measurement, 1.3 ml of RT reagent (25 mg OPA, 25 mg thioglycolate in 1 ml methanol, pH to 10.4 with 10 ml 0.4 M sodium borate buffer) were pipetted into the 1.5 ml fluorescence cuvette (Plastibrand®, Brand) the base line/value was adjusted to zero. Subsequently, 20 µl of cell-free sample were mixed with the reagent and the reaction process was followed. The maximum emission intensity valued was noted. In order to determine ammonium concentration in the sample, a reference value (standard solution 5.56 mM ammonium) was measured, accordingly. The concentration of the ammonium in the sample was determined with the following relation:

$$c_{smpl} = I_{smpl} \cdot \frac{c_{std}}{I_{std}} \qquad (10.9)$$

$c_{smpl}$ concentration of ammonium in the sample $\left[\frac{mol}{L}\right]$ $c_{std}$ concentration of ammonium in the standard $\left[\frac{mol}{L}\right]$ $I_{smpl}$ maximum emission intensity of the sample —

$I_{std}$ maximum emission intensity of the standard —

Determination of Osmolality

The osmolality of supernatants were measured using the freezing point depression osmometer (Osmomat Auto, Gonotech GmbH). The samples measurement was performed with 150 µl cell-free supernatant. Osmolality values were expressed in mOsmol Kg. A two point calibration was done with MilliQ-H$_2$O (0 mOsmol/kg) and a standard solution with predefined osmolality (280 mOsmol/kg or 320 mOsmol/kg; Gonotech GmbH).

Determination of Product Concentration

The concentration of the recombinant protein was carried out by size-exclusion-high performance-liquid-chromatography (SEC-HPLC) by the technical personal from AG Cell Culture Technology.

Dissolved Gas Analysis

The quantitative measurement of pH value and CO$_2$ concentrations was performed with the automatic blood gas analyzer AVL COMPACT 3 (Roche Diagnostics GmbH, Mannheim, Germany). A volume of 100 µl sample is necessary for the measurement. The CO$_2$ (%) was calculated by the Equation 10.10.

$$x_{CO2} = 100 \cdot \frac{p_{CO2}}{P_t} \qquad (10.10)$$

$x_{CO2}$ concentration of CO$_2$ [%]

$p_{CO2}$ partial pressure of CO$_2$ [mmHg]

$P_t$ Total pressure [mmHg]

Flow Cytometry

The flow cytometric analyses was carried out with a FACSCALIBUR™ flow cytometer (Becton Dickinson) using an argon laser with an excitation wavelength of 488 nm. Data acquisition and analysis was carried out using a G4 Apple Macintosh computer with the CELLQUEST™ Pro software. Forward light scatter (FCS) and sideward scatter (SSC) were used to examine the size and granularity of the cells.

Intracellular pH Measurement pHi measurements were carried out by flow cytometry with the available pHi fluorescent indicator, Carboxy SNARF-1 AM (Molecular Probes Inc.). This dye is an acetoxymethyl (AM) ester that enter the cells readily and is hydrolyzed by non-specific esterases to yield the free fluorescent dye. SNARF-1 AM is very sensitive to pHi changes within the physiological range. It is excited between 488 nm and 530 nm and the fluorescence emission is monitored at two wavelengths, typically about 580 nm (FL2-H) and 640 nm (FL3-H). This is particularly interesting as the fluorescence emission wavelength ratio can be calculated foe a more accurate determination of the pHi. With the use of this ratiometric technique, a number of fluorescence measurement artifacts are eliminated, such as photobleaching, cell thickness and leakage and non-uniform loading of the indicator (SNARF® pH indicators, Product information, 2003, Molecular Probes Inc.). Herein the Pseudo-Null calibration method was used. The method is based on the assumption that (i) only the non-ionized forms of the weak acid or base can cross the cell membrane, (ii) the dissociation constants, pKa and pKb, are the same inside and outside of the cell, and (iii) mechanisms that regulate pHi do not influence the critical changes in pHi (or fluorescence) observed. A simplification can be considered if the calibration solutions are prepared in such a way that a concentration of weak base and a concentration of weak acid produce an equal but opposite change in pHi (i.e., pHa=pHb). The derived relationship for pHi determination is presented in Equation 10.11.

$$pH_i = pH_e - 0.5 \log\left(\frac{[A]}{[B]}\right) \qquad (10.11)$$

$pH_i$ intracelluar pH —

$pH_e$ extracellular pH —

[A] concentration of weak acid [mM]

[B] concentration of weak base [mM]

Where the pHi is dependent on the extracellular pH value (pHe) and on the ratio of concentration of weak base (B) and weak acid (A) present in the solution. The ratio of weak acid and base that gives no change in pHi could be extrapolated between those that lead to the smallest increase in pHi ("Null Point"). If the molar concentration of the acid-base ratio is sufficient, then no further addition of acid to base in the same ratio causes a change in the pHi, so that value reflected a new null value (designated Pseudo-Null) that satisfies Equation 10.11. Therefore, a calibration curve can be obtained from the plot of pseudo-null pH value vs. fluorescence ratio by exposing cells to a series of acid-to-base mixtures at sufficient molar concentration. Those mixtures were done with butyric acid (BA) and trimethylamine (TMA) (Table 3). The preparation of calibration solutions was done in HEPES buffer containing FBS (named HDFBS buffer; following Table). The addition of FBS aids maintenance of the cells physiological conditions.

TABLE

| Buffer/Solution | Composition |
| --- | --- |
| Carboxy SNARF-1 AM | dissolve in DMSO at 2 μM store at 4° C. |
| HEPES buffer | 10 mM HEPES<br>133.5 mM NaCl<br>4 mM KCl<br>1.2 mM $NaH_2PO_4 \cdot H_2O$<br>1.2 mM $MgSO_4$<br>11 mM α-D-glucose<br>2 mM $CaCl_2 \cdot 2H_2O$<br>adjust pH to 7.4 |
| HDFBS buffer | 90% (v/v) HEPES buffer<br>10% (v/v) FBS |
| Butyric acid (BA) | 1M n-butyric acid (pKa 4.82)<br>adjust pH to 7.4 |
| Trimethylamine (TMA) | 1M trimethylamine (pkb 9.8)<br>adjust pH to 7.4 |

A 5 ml disposable syringe was pre-loaded with 22 μl of SNARF-1 AM (2 mM in DMSO). Subsequently, 2.5 ml samples were taken from a bioreactor, the syringe was closed with a Luer-stopper (Rotilabo) and cells were stained for 25 min. at 37° C. Afterwards, 200 μl of stained cells were mixed with 200 μl of 37° C. HDFBS buffer and measured with the FACS. Samples were analyzed in replicates. Emission fluorescence was measured at 580 nm (FL2-H) and 640 nm (FL3-H).

Calibration curves were established with the same sampled stained cells. Hence, six times concentrated standard solutions were prepared by adding different amounts of butyric acid (BA) and trimethylamine (TMA) to the HBFBS buffer, as shown in the following Table.

TABLE

| Buffer | 6x concentration<br>BA/TMA (mM) in HDFBS Buffer, pH 7.4 | Pseudo Null pH |
| --- | --- | --- |
| S1 | 6/96 | 8.0 |
| S2 | 6/24 | 7.7 |
| S3 | 6/6 | 7.4 |
| S4 | 24/6 | 7.1 |
| S5 | 96/6 | 6.8 |

A volume of 200 μl of each solution was pipetted into the polypropylene tubes, closed with a cap to avoid evaporation and incubated at 37° C. Calibration was achieved by mixing 200 μl of dye-loaded cells and 200 μl of aliquoted and pre-warmed 6x calibration solution. Flow cytometry acquisition began after 20 sec. in "HIGH RUN" modus and 10,000 total events were analyzed. Prior to flow cytometric analysis, two calibration mixtures with cells were measured with the blood gas analyzer to obtain the exact external pH value. The emission fluorescence ratios, 640 nm/580 nm, were calculated with the program FCSassist™ 1.0. Further data analysis was executed with the CellQuest™ Pro software. Cells that failed to retain SNARF-1 fluorescence were gated out on the fluorescence histograms. From the histogram FL3-H/FL2-H vs. counts analysis a histogram statistic was made and the mean fluorescence value was noted. With the information of the true external pH of the calibration samples, the induced pHi was calculated using the Equation 10.11. The mean fluorescence ratio of each standard was plotted against calculated induced pHi. The samples pHi was derived from the curve.

Re-Alkalinization Experiment

The regulation of the pHi was studied by flow cytometric analysis during intracellular acidification with bicarbonate. The kinetic of the transporters were examined. This test was made at physiological conditions. Therefore medium was used instead of buffer to account for influences of other medium components. To eliminate the activity of other cellular pHi-regulation systems, cells were pre-incubated in bicarbonate-free medium buffered with HEPES. A closed system was built to avoid $CO_2$ degassing that could cause pHe changes and, hence ensuing pHi alterations. This system consisting of two disposable 5 ml Luer-Lock syringes (B. Braun AG, Melsungen, Germany) connected by a short tubing and two Luer tubing connectors (Rotilabo®). These Luer connectors permitted the rapid and easy connection/disconnection of the 2 syringes.

Syringe A contained stained cells in bicarbonate-free production medium and syringe B production medium with 4.2 g/l $NaHCO_3$ (corresponding to 25% $CO_2$ at pH 7.2). Both media contained 20 mM HEPES and were adjusted to pH 7.2 at 37° C. Acid-load was achieved by pressing bicarbonate-containing medium from syringe B into syringe A. A 5 ml syringe was pre-loaded with 22 μl of SNARF-1 AM (2 mM stock solution; Table 3). $1 \times 10^6$ cells, from the exponential phase, were harvested and washed once with 4 ml medium without bicarbonate. After which, the cell suspension was sucked (without air bubbles) into the pre-loaded fluorescence dye syringe, which was them closed with the Luer-stopper and gently mixed. After a 25 min. period of incubation at 37° C. in the dark, with regularly mixing to avoid cell settling, followed dissolved gas and flow cytometric analysis. Three measurements of loaded cells in bicarbonate-free medium were made before acidification of cells cytoplasm. Afterwards, the syringe B was connected to syringe A and the double volume of $NaHCO_3$-containing medium was added. The syringe B was discarded, syringe A was closed and after short mixing, the acid-loaded cells were analyzed by flow cytometry. Additionally, some samples were measured with the blood gas analyzer to determine the content of $CO_2$ in medium during the experiment.

To test if the re-alkalinization effect was due to the hCAII-overexpression, the hCAII inhibitor ethoxyzolamide (ACTZ) was used. For the hCAII inhibited experiments, media with 100 μM ethoxyzolamide (stock solution: 100 mM ACTZ in DMSO stored at 4° C.) was used. The experiment procedure was the same as described above.

Cell Cycle

Herein the deoxyribonucleic acid (DNA) content has been determined for cell cycle analysis. Samples were taken every 24 h until viability decreased below 60%. Approximately $1 \times 10^6$ cells were harvested and two times washed with cold-PBS by centrifugation (200×g, 10 min., RT). Cells were then fixed and permeabilized with 1 ml ice-cold 70% ethanol and kept at −20° C. until staining Before staining, cells were spun down followed by washing with PBS/0.1% Saponin. Cells were then stained with 1 ml staining solution (PBS/0.1% Saponin, 40 µg/ml RNAse S, 20 µg/ml PI) by incubation in the dark for 45 min. at room temperature. The RNA degradation reaction was stopped by incubating the stained cells on ice until flow cytometric analysis. Data was acquired with "LOW RUN" modus at a flow rate <200 cells/sec. The G0G1 cell fraction was acquired on channel 200 of FL3-H (640 nm) histogram. The integral fluorescence of the cells was analyzed by the computer software Mod-Fit™ LT (Becton Dickinson) to obtain the percentages of cells in the G0G1-, S-, and G2M-phase.

Protein Extraction

For Western Blot

About $1 \times 10^7$ cells were harvested and washed two times with cold PBS. The cell pellet was resuspended in 600 µl lysis buffer (RIPA buffer, see following Table) and incubated for 5 min. on ice. The lysis proceeds with a 5 min. sonication step followed by a 30 min. incubation step on ice. The lysate was subsequently centrifuged for 30 min. at 16,200×g and 4° C. to remove cell debris. The protein solution was stored at −20° C.

TABLE

| Buffer/Solution | Composition |
| --- | --- |
| Lyse buffer | 50 mM Tris-HCl (pH 7.2) |
| | 2 mM EDTA |
| | 150 mM NaCl |
| | 1% (v/v) NP-40 |
| | 1 mM PMSF (add freshly from stock solution) |
| | 0.1% (w/v) SDS |
| RIPA buffer | 50 mM Tris-HCl (pH 8.0) |
| | 150 mM NaCl |
| | 5 mM EDTA |
| | 1 mM PMSF (add freshly from stock solution) |
| TE buffer | 10 mM Tris-HCl (pH 8.8) |
| | 1 mM EDTA |
| | 2 mM PMSF (add freshly) |
| PMSF stock solution | 100 mM phenylmethylsulphonyl fluoride in isopropanol |
| DNase/RNase-mix stock solution | 1 mg/mL DNase |
| | 0.25 mg/mL RNase |
| | 50 mM $MgCl_2$ |

For hCAII Activity

Protein extraction was performed with RIPA Buffer (see previous Table). About $1 \times 10^7$ cells were harvested and two times washed with cold PBS. The resulting pellet was resuspended in 2 ml RIPA buffer and solution was frozen at −80° C. for 2 h. After thawing on ice, cell suspension was treated for 15 sec. with an Ultrasonic finger (Sonifier 250, Branson). Cell debris was spun down (17,000×g, 1 h, 4° C.) and cytosolic proteins were stored at −20° C. until carbonic anhydrase activity measurements.

For Proteomic Analysis $1 \times 10^8$ cells were harvested from the bioreactor at cultivation day 2 (before $CO_2$ profile) and 4 (two days after $CO_2$ profile had started) for both cell lines (clone E11 and control cell line in HyQ medium). Cells were washed with cold PBS (200×g, 10 min.) and pellet was stored at −80° C. until cell lysis. The frozen cell pellet was resuspended in 1 ml TE-buffer (see Table above). Subsequently, 20 µl of a serine protease inhibitor stock solution, phenyl methylsulphonyl fluoride (PMSF), and 100 µl of a DNAse/RNAse-mix stock solution was added (see Table above). After transferring the cells in solution to a 2 ml vessels containing 1 g glass beads (about 0.15 mm; BioSpec Products Inc.), the mechanical cell disruption was carried out with four homogenization cycles performed in a vortex, from 30 sec. each. Between each cycle, the cells were stored on ice. Afterwards, proteins in solution were separated from the cells debris and glass beads by a centrifugation step (16,200×g, 20 min., 4° C.). For the separation of the proteins in solution and cells compartments, an ultracentrifugation at 106,000×g for 1 h at 4° C. (Optima™ L-90K, Beckman Coulter Inc., USA) was performed. To determine the protein content of the supernatant part of the protein extract was removed to perform a BCA assay. The rest of the protein solution was stored at −20° C.

Determination of Protein Concentration

The determination of protein concentration was performed by the bicinchoninic acid (BCA) method using the protein quantification kit (Uptima/Interchim). It involves the reduction of Cu(II) to Cu(I) by peptidic bounds of proteins. The bicinchoninic acid chelates Cu(I) ions with very high specificity to form a water soluble purple colored complex. The reaction is measured at 562 nm, corresponding to the high optical absorbance of the final Cu(I) complex. The protein concentration is proportional to the absorbance. It was followed the protocol described by the manufacturer with a standard curve between 20 and 2,000 µg/ml of Bovine Serum Albumin (BSA). Samples and standard were diluted in the corresponding lysis buffer. The absorption was measured with the Photospectrometer PowerWave™ HT (BioTek Instruments). The quantification was performed with the Software KC4 (BioTek Instruments).

Acetone Precipitation

Aliquots of 10 µg or 40 µg and 150 µg or 450 µg were prepared for western blotting. Therefore, one volume of sample was mixed with 9 volumes of ice cold acetone. Subsequently, the sample was incubated overnight at −20° C. After centrifugation (16,200×g, 30 min., 4° C.) to pellet the precipitated protein, the supernatant was removed and the undesired acetone was allowed to evaporate at RT. The dried protein pellet was stored at −20° C.

SDS-PAGE

Preparation of gel electrophoresis module and gel cassette was performed according to manufacturers' instructions (Invitrogen). The protein sample pellets to be analyzed and 20 µg the positive control (carbonic anhydrase isozyme II from human erythrocytes, 1 mg/ml, Sigma Aldrich) were mixed with sample buffer (4×, NuPAGE®), reducing agent (10×, Invitrogen) and MilliQ-$H_2O$ to a final volume of 20 µl. The denaturation of the secondary and tertiary structures and the reduction (cleaving of disulphide bonds between cysteine residues) of proteins was achieved by incubating samples at 70° C. for 10 min. in a thermoblock. Finally, the samples and 5 µl of the molecular weight marker (SeeBlue® Plus2 Pre-stained standard, 4 kDa to 250 kDa; Invitrogen) were loaded into the 10% NuPAGE® Novex Bis-Tris Gel (Invitrogen) slots. The gel was run with NuPAGE® MOPS SDS running buffer, furthermore, reducing condition were achieved with 0.25% (v/v) antioxidant reagent in running buffer in the middle of the electrophoresis camera. The gel run in the XCell™ Sure Lock system (Invitrogen) at 200 V until bromophenol reached the end of the gel.

Western Blot

The solutions necessary for this experiment are described in the following Table.

TABLE

| Buffer/Solution | Composition |
| --- | --- |
| Transfer buffer | 1x NuPAGE ® Transfer buffer (20x) |
| | 0.001% (v/v) NuPAGE ® Reducing agent |
| | 10% (v/v) Methanol |

TABLE-continued

| Buffer/Solution | Composition |
|---|---|
| Washing solution | 0.3% (w/v) Milk pulver<br>0.3% (v/v) Tween 20<br>in PBS |
| Blocking solution | 3% (w/v) Milk pulver in washing solution |
| Antibody solution | 1% (w/v) Milk pulver in washing solution |

Following SDS-PAGE, the separated proteins were transferred from the gel to a thin Hybond™P PVDF-membrane. Prior to this, the membrane was previously in methanol wetted (30 sec.) and equilibrated in transfer buffer. The XCell II™ Blot Module was set up according to the manufacturers instructions. Transfer buffer was added to the inside of the Blotting Module and MilliQ-$H_2O$ to the outer part. The blotting was carried out at a constant voltage of 35 V for 1 h. Afterwards, the membrane was blocked in 20 ml blocking solution (1 h, shaking, RT), in order to prevent unspecific antibody binding in the following steps. After washing the membrane twice, the carbonic anhydrase II was detected in a three-step procedure. In the first step, the membrane was incubated (4° C.) with a 1:50,000 or 1:20,000 specific primary antibody diluted solution (Rabbit polyclonal IgG to CAII, 10 mg/ml, Abcam) overnight. In a second incubation step (1 h, RT), 1:4,000 peroxidase-conjugated secondary antibody diluted solution (ECL™ Donkey anti-rabbit IgG, HRP-Linked, 0.20 mg/ml, GE Healthcare) was applied. In a final step, the membrane was exposed to the ECL™ Plus Western Blotting Reagent (Amersham), and the qualitative analysis was done by means of enhanced chemiluminescence (ECL) and autoradiography ECL-films (Hyperfilm™ ECL™ film, Amersham), according to manufacturer's instructions. Between the incubations with the different antibodies and before detection, the membrane was washed shortly with washing solution, followed by two 15 min washing steps. All washing steps were performed at RT while shaking. Film exposure times ranged from 30 sec to 5 min. Afterwards, films were developed until protein band had a good resolution, followed by a short washing step in MilliQ-$H_2O$ and fixation for about 10 min. Later, the films were watered for about 30 min. and finally dried.

Carbonic Anhydrase Activity

The activity of carbonic anhydrase in lysates was determined using the $^{18}O$ exchange method developed by SILVERMAN (SILVERMAN, D. N., Methods Enzymol. 87 (1982) 732-752). The $^{18}O$ exchange method is based on the assessment by membrane-inlet mass spectrometry of the exchange of $^{18}O$ between $CO_2$ and water at chemical equilibrium (Equations 10.12 and 10.13).

(10.12)

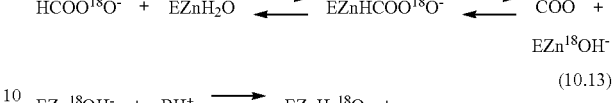

(10.13)

Lysates from control cell lines and from clones G9 and E11 were prepared by two different approaches. One of them focused on the cytoplasm protein extraction in RIPA buffer and the other on the protein extraction by mechanical disruption with glass beads in TE buffer. As positive control, the commercial available carbonic anhydrase II (carbonic anhydrase isozyme II from human erythrocytes; Sigma Aldrich) was used. The lysates were divided into two aliquots and the positive control was added to one of the samples in order to exclude influence of buffer composition and other proteins in the determination of CAII activity. The total enzyme concentration of a solution containing the positive control was computed using a linear regression fitting to the inhibition data for the titration curve with highly CAII bound inhibitor ethoxyzolamide (EZA). This value was used as standard for the calculation of the CAII concentration in the samples using Equation 10.14.

$$c_{smpl} = \frac{Act_{smpl}}{Act_{std}} \cdot \frac{V_{std}}{V_{smpl}} \cdot c_{std} \quad (10.14)$$

$c_{smpl}$ concentration of CAII in the sample $\left[\frac{\mu mol}{L}\right]$ $c_{st}$ concentration of CAII in the standard $\left[\frac{\mu mol}{L}\right]$ $Act_{smpl}$ activity of CAII in the sample —

$Act_{std}$ activity of CAII in the standard —

$V_{smpl}$ volume of sample used for measurement μL $V_{std}$ volume of standard used for measurement μL

---

What is claimed is:

1. A method for recombinantly producing a polypeptide in a mammalian host cell, comprising the following steps:
   a) cultivating the mammalian host cell transfected with a first polynucleotide encoding a carbonic anhydrase and a second polynucleotide encoding the polypeptide, and
   b) recovering the polypeptide from the host cell or the cultivation medium and thereby producing the polypeptide, wherein the carbonic anhydrase is a human carbonic anhydrase II having the amino acid sequence of SEQ ID NO:3.

2. The method according to claim 1, wherein the cultivating comprises a first period of time with a first constant $pCO_2$ value, and thereafter a second period of time with an increasing $pCO_2$ value from the first constant $pCO_2$ value to a second $pCO_2$ value.

3. The method according to claim 2, wherein the first constant $pCO_2$ value is of from about 4% to about 9%.

4. The method according to claim 3, wherein the first constant $pCO_2$ value is about 5%.

5. The method according to claim 2, wherein the second $pCO_2$ value is of from about 15% to about 30%.

6. The method according to claim 5, wherein the second $pCO_2$ value is about 25%.

7. The method according to claim 2, wherein the cultivating further comprises a third period of time after the second period of time with the same $pCO_2$ value as the second $pCO_2$ value.

8. The method according to claim 1, wherein the polypeptide is an antibody, or an antibody conjugate, or an antibody fragment, or an Fc-region fusion polypeptide.

9. The method according to claim 1, wherein the mammalian host cell is a CHO cell.

10. The method according to claim 9, wherein the CHO cell is a CHO K1 cell.

* * * * *

SEQUENCE LISTING

```
<160> NUMBER OF SEQ ID NOS: 5

<210> SEQ ID NO 1
<211> LENGTH: 1666
<212> TYPE: DNA
<213> ORGANISM: Homo sapiens

<400> SEQUENCE: 1 cctcccttg tcgcctaggt ccacccgagc ccctccccc gggccgcccc cgagcacgaa      60
gttggcggga gcctataaaa gctggtgccg gcgcgacccg cggacacaca gtgcaggcgc     120
ccaagccgcc gccgccagat cggtgccgat tcctgccctg ccccgaccgc cagcgcgacc    180
atgtcccatc actgggggta cggcaaacac aacggacctg agcactggca taaggacttc    240
```

```
cccattgcca agggagagcg ccagtcccct gttgacatcg acactcatac agccaagtat      300
gaccctcccc tgaagcccct gtctgtttcc tatgatcaag caacttccct gaggatcctc      360
aacaatggtc atgctttcaa cgtggagttt gatgactctc aggacaaagc agtgctcaag      420
ggaggacccc tggatggcac ttacagattg attcagtttc actttcactg gggttcactt      480
gatggacaag gttcagagca tactgtggat aaaaagaaat atgctgcaga acttcacttg      540
gttcactgga acaccaaata tggggatttt gggaaagctg tgcagcaacc tgatggactg      600
gccgttctag gtatttttt gaaggttggc agcgctaaac cgggccttca gaaagttgtt       660
gatgtgctgg attccattaa acaaagggc aagagtgctg acttcactaa cttcgatcct       720
cgtggcctcc ttcctgaatc cttggattac tggacctacc caggctcact gaccacccct      780
cctcttctgg aatgtgtgac ctggattgtg ctcaaggaac ccatcagcgt cagcagcgag      840
caggtgttga attccgtaa acttaacttc aatggggagg gtgaacccga agaactgatg       900
gtggacaact ggcgcccagc tcagccactg aagaacaggc aaatcaaagc ttccttcaaa      960
taagatggtc ccatagtctg tatccaaata atgaatcttc gggtgtttcc ctttagctaa     1020
gcacagatct accttggtga tttggaccct ggttgctttg tgtctagttt tctagaccct     1080
tcatctctta cttgatagac ttactaataa aatgtgaaga ctagaccaat tgtcatgctt     1140
gacacaactg ctgtggctgg ttggtgcttt gtttatggta gtagttttc tgtaacacag      1200 aatataggat aagaaataag aataaagtac cttgactttg ttcacagcat gtagggtgat     1260
gagcactcac aattgttgac taaaatgctg cttttaaaac ataggaaagt agaatggttg     1320
agtgcaaatc catagcacaa gataaattga gctagtaag gcaaatcagg taaaatagtc      1380
atgattctat gtaatgtaaa ccagaaaaaa taaatgttca tgatttcaag atgttatatt     1440
aaagaaaaac tttaaaaatt attatatat tatagcaaag ttatcttaaa tatgaattct      1500
gttgtaattt aatgactttt gaattacaga gatataaatg aagtattatc tgtaaaaatt     1560
gttataatta gagttgtgat acagagtata tttccattca gacaatatat cataacttaa     1620
taaatattgt attttagata tattctctaa taaaattcag aattct                   1666
```

<210> SEQ ID NO 2
<211> LENGTH: 260
<212> TYPE: PRT
<213> ORGANISM: Homo sapiens

<400> SEQUENCE: 2

```
Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
                20                  25                  30

Ile Asp Thr His Thr Ala Lys Tyr Asp Pro Ser Leu Lys Pro Leu Ser
            35                  40                  45

Val Ser Tyr Asp Gln Ala Thr Ser Leu Arg Ile Leu Asn Asn Gly His
        50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125
```

```
Asp Phe Gly Lys Ala Val Gln Gln Pro Asp Gly Leu Ala Val Leu Gly
            130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Leu Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260

<210> SEQ ID NO 3
<211> LENGTH: 260
<212> TYPE: PRT
<213> ORGANISM: Artificial Sequence
<220> FEATURE:
<223> OTHER INFORMATION: hCAII mutant S2A

<400> SEQUENCE: 3

Met Ala His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
            130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Leu Lys
    210                 215                 220
```

```
Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260

<210> SEQ ID NO 4
<211> LENGTH: 22
<212> TYPE: DNA
<213> ORGANISM: Artificial Sequence
<220> FEATURE:
<223> OTHER INFORMATION: primer 1

<400> SEQUENCE: 4
ggtttagtga accgtcagat cc                                              22

<210> SEQ ID NO 5
<211> LENGTH: 22
<212> TYPE: DNA
<213> ORGANISM: Artificial Sequence
<220> FEATURE:
<223> OTHER INFORMATION: primer 2

<400> SEQUENCE: 5
aaagggcaag agtgctgact tc                                              22
```